(12) United States Patent
Buttermann et al.

(10) Patent No.: US 10,045,802 B2
(45) Date of Patent: Aug. 14, 2018

(54) ORTHOPAEDIC DEVICE

(71) Applicant: DYNAMIC SPINE, LLC, Mahtomedi, MN (US)

(72) Inventors: Glenn R. Buttermann, Mahtomedia, MN (US); Frank R. Ferris, Jr., Bellevue, WA (US)

(73) Assignee: DYNAMIC SPINE, LLC, Mahtomedi, MN (US)

( * ) Notice: Subject to any disclaimer, the term of this patent is extended or adjusted under 35 U.S.C. 154(b) by 454 days.

(21) Appl. No.: 14/436,029

(22) PCT Filed: Oct. 15, 2012

(86) PCT No.: PCT/US2012/060239
§ 371 (c)(1),
(2) Date: Apr. 15, 2015

(87) PCT Pub. No.: WO2014/062154
PCT Pub. Date: Apr. 24, 2014

(65) Prior Publication Data
US 2015/0272637 A1    Oct. 1, 2015

(51) Int. Cl.
*A61B 17/80* (2006.01)
*A61B 17/17* (2006.01)
(Continued)

(52) U.S. Cl.
CPC .......... *A61B 17/80* (2013.01); *A61B 17/1728* (2013.01); *A61B 17/7059* (2013.01);
(Continued)

(58) Field of Classification Search
CPC ............. A61B 17/80–17/8095; A61B 17/1728
See application file for complete search history.

(56) References Cited

U.S. PATENT DOCUMENTS 4,827,918 A * 5/1989 Olerud ............... A61B 17/7014
403/116
5,364,399 A * 11/1994 Lowery .............. A61B 17/1728
606/286

(Continued)

FOREIGN PATENT DOCUMENTS

WO WO-2008/064211 A1 5/2008
WO WO 2012112444 A1 * 8/2012 ......... A61B 17/1757

OTHER PUBLICATIONS

International Search Report dated Jan. 18, 2013, issued in PCT Application No. PCT/US2012/060239, filed Oct. 15, 2012.
(Continued)

*Primary Examiner* — Zade Coley
(74) *Attorney, Agent, or Firm* — Foley & Lardner LLP

(57) ABSTRACT

An orthopedic device for repairing a portion of a body, the orthopedic device includes an orthopedic plate, a tissue protector, and a rotating member. The orthopedic plate is configured to attach to at least one bone. The tissue protector is attached to the orthopedic plate and configured to at least partially detach from the orthopedic plate after a force is applied to the tissue protector. The rotating member is configured to connect the tissue protector to the orthopedic plate while allowing the tissue protector to rotate relative to the orthopedic plate.

11 Claims, 27 Drawing Sheets

(51) Int. Cl.
*A61B 17/70* (2006.01)
*A61B 17/86* (2006.01)
*A61B 90/00* (2016.01)

(52) U.S. Cl.
CPC ........ *A61B 17/863* (2013.01); *A61B 17/8057* (2013.01); *A61B 2090/037* (2016.02); *A61B 2090/08021* (2016.02)

(56) References Cited

U.S. PATENT DOCUMENTS

| | | | | |
|---|---|---|---|---|
| 6,235,034 | B1* | 5/2001 | Bray | A61B 17/1655 606/246 |
| 6,261,039 | B1* | 7/2001 | Reed | B23P 6/04 411/178 |
| 7,101,398 | B2 | 9/2006 | Dooris | A61F 2/08 606/151 |
| 7,303,564 | B2* | 12/2007 | Freid | A61B 17/7059 606/247 |
| 7,357,804 | B2* | 4/2008 | Binder, Jr. | A61B 17/1728 606/96 |
| 7,488,327 | B2* | 2/2009 | Rathbun | A61B 17/1728 606/96 |
| 8,523,862 | B2* | 9/2013 | Murashko, Jr. | A61B 17/1728 408/115 R |
| 2002/0029040 | A1* | 3/2002 | Morrison | A61B 17/7007 606/292 |
| 2002/0082606 | A1* | 6/2002 | Suddaby | A61B 17/1728 606/96 |
| 2005/0070899 | A1* | 3/2005 | Doubler | A61B 17/8869 606/264 |
| 2005/0228398 | A1* | 10/2005 | Rathbun | A61B 17/1728 606/96 |
| 2005/0234467 | A1* | 10/2005 | Rains | A61B 17/1735 606/96 |
| 2006/0084980 | A1 | 4/2006 | Melkent et al. | |
| 2006/0149250 | A1* | 7/2006 | Castaneda | A61B 17/1728 606/86 B |
| 2006/0200147 | A1* | 9/2006 | Ensign | A61B 17/8047 606/281 |
| 2006/0235410 | A1* | 10/2006 | Ralph | A61B 17/686 606/313 |
| 2006/0264962 | A1* | 11/2006 | Chin | A61B 17/7037 606/90 |
| 2008/0039838 | A1* | 2/2008 | Landry | A61B 17/1604 606/86 A |
| 2009/0012571 | A1* | 1/2009 | Perrow | A61B 17/1671 606/280 |
| 2009/0118770 | A1* | 5/2009 | Sixto, Jr. | A61B 17/8061 606/280 |
| 2009/0157121 | A1* | 6/2009 | Harris | A61B 17/8695 606/280 |
| 2010/0106196 | A1* | 4/2010 | Erickson | A61B 17/1728 606/281 |
| 2012/0071934 | A1* | 3/2012 | Brandon | A61B 17/1615 606/286 |
| 2012/0253347 | A1* | 10/2012 | Murashko, Jr. | A61B 17/1728 606/71 |

OTHER PUBLICATIONS

Supplementary European Search Report dated Sep. 2, 2016, received in corresponding European application No. 12 88 6871, 9 pages.

Office Action dated May 14, 2018, received in corresponding Canadian application No. 2,927,433, 3 pages.

* cited by examiner

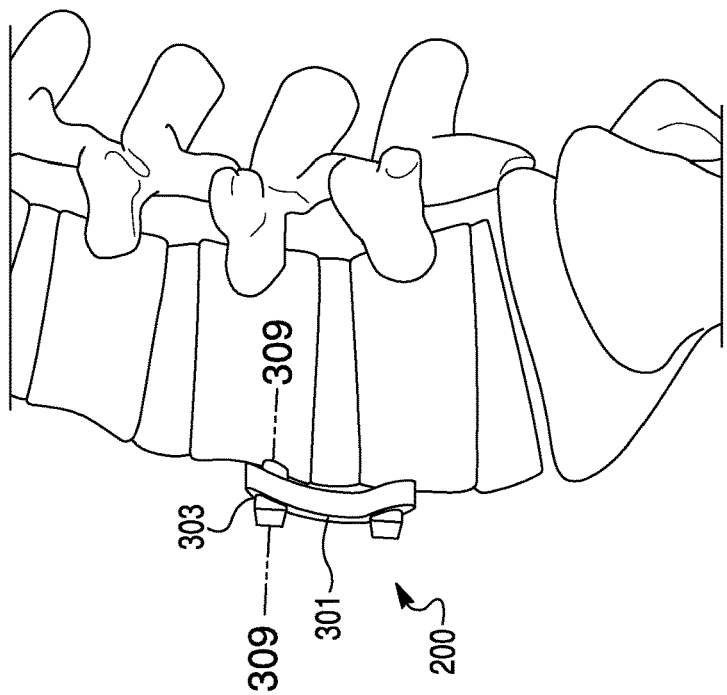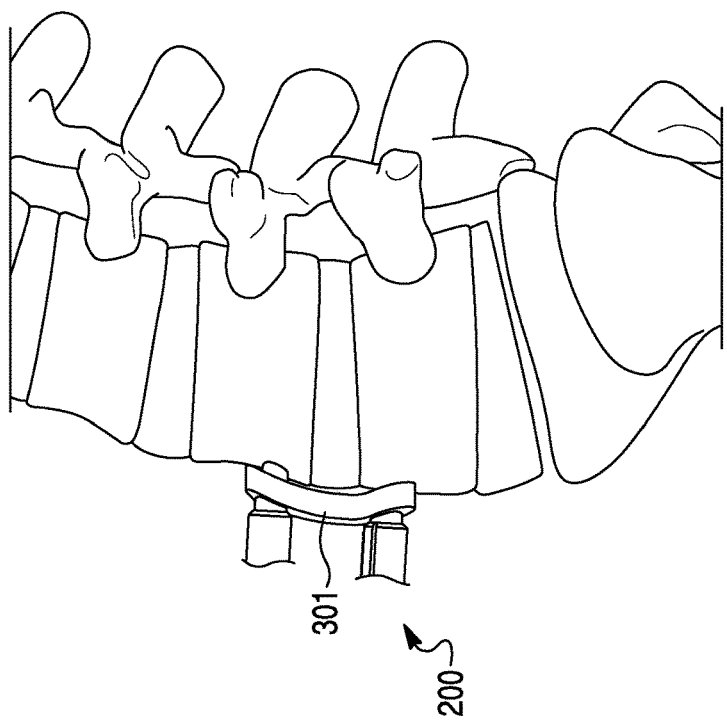

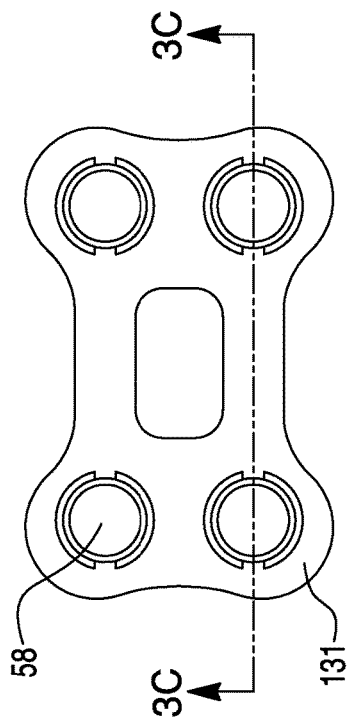
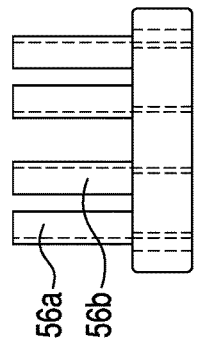
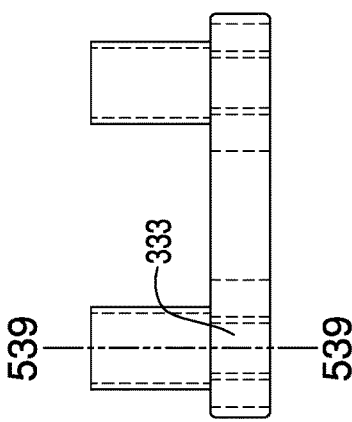
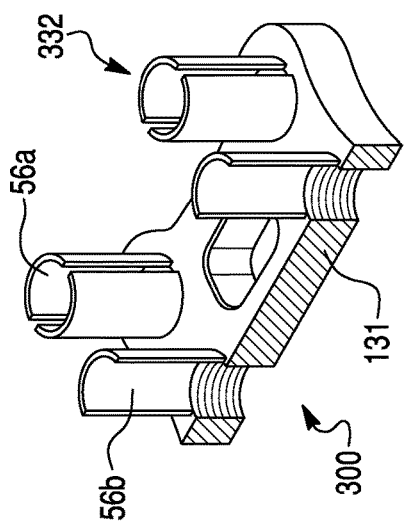
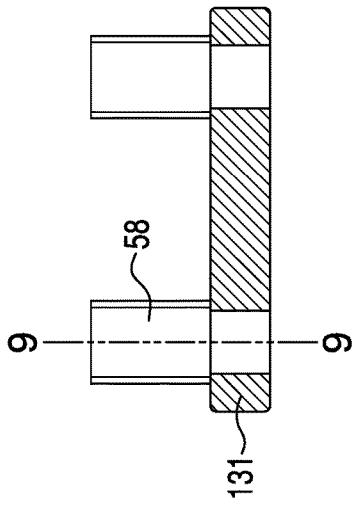

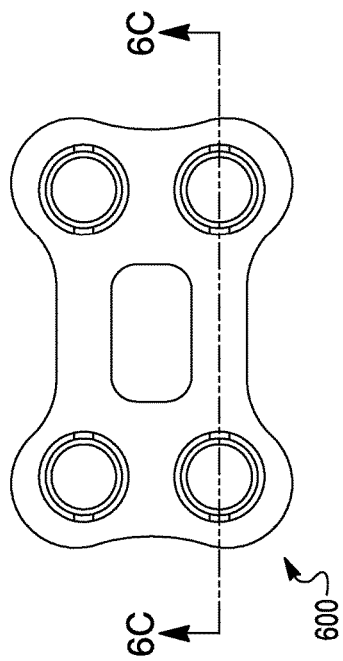
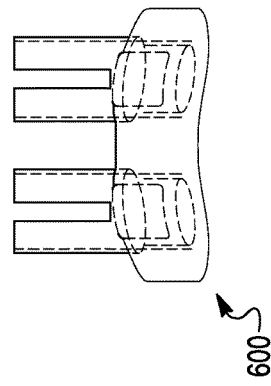
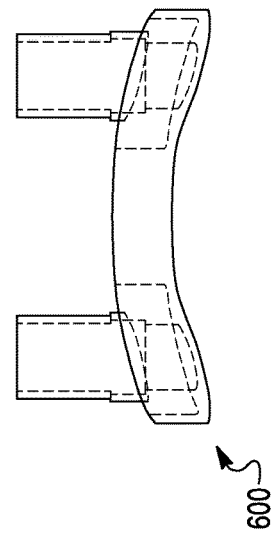
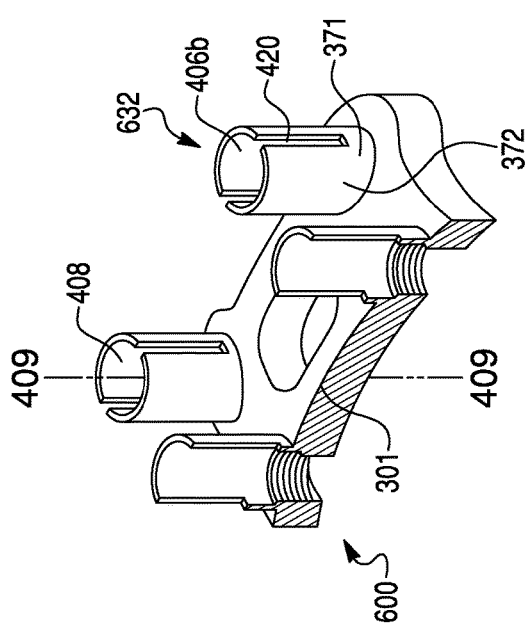
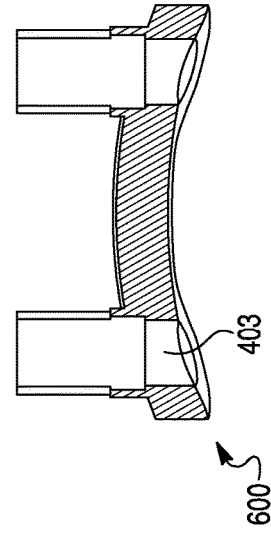

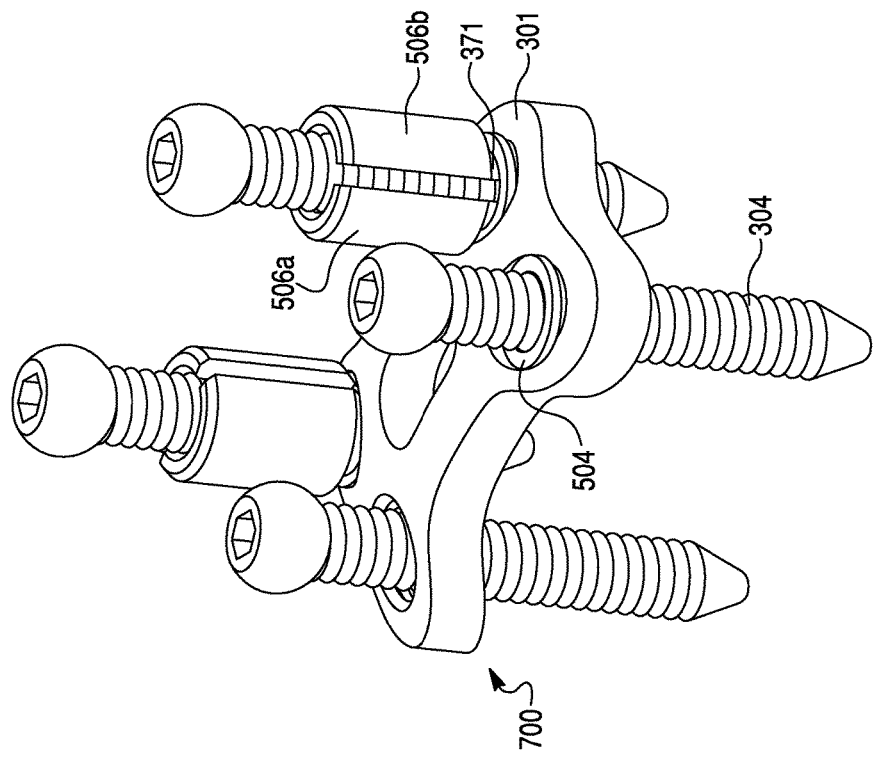
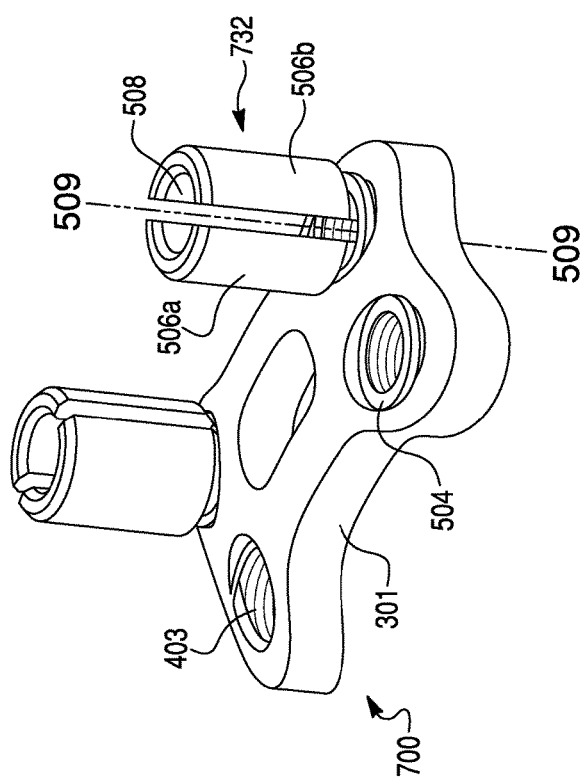
Figure 7B
Figure 7A

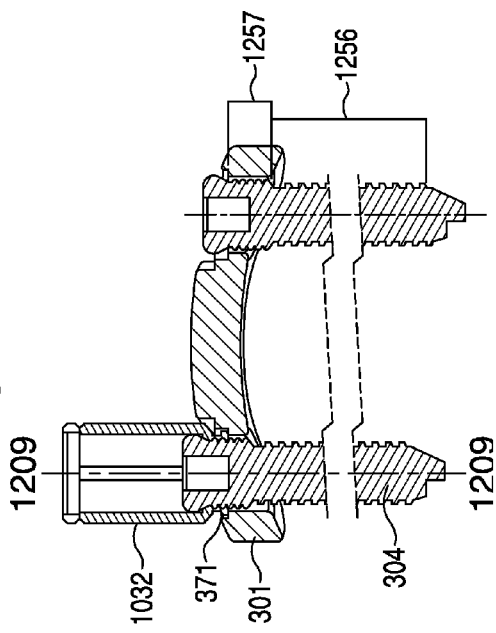
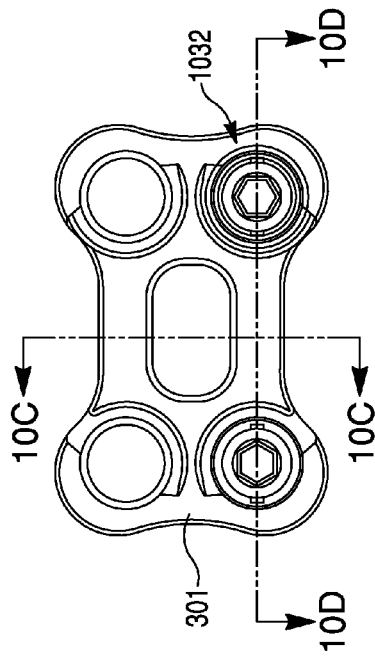
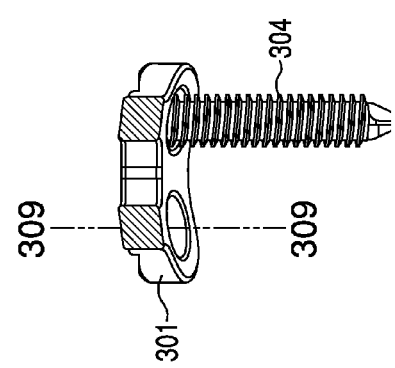
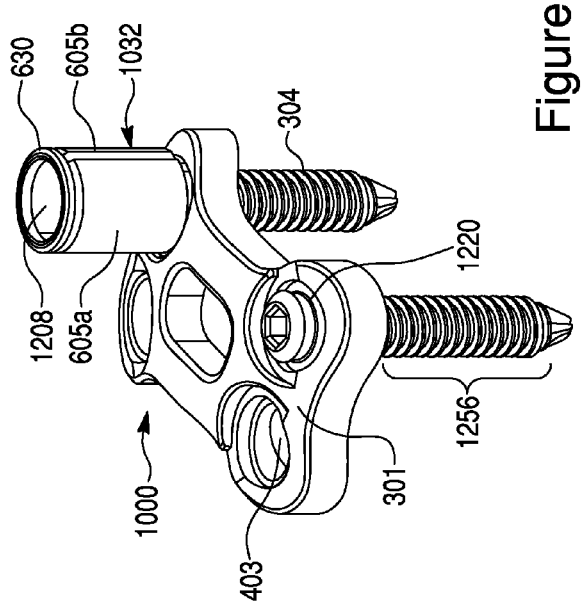

ORTHOPAEDIC DEVICE

BACKGROUND

Field of Embodiments

The disclosed embodiments relate generally to an orthopaedic device having an orthopaedic plate and a tissue protector.

Description of Related Art

During the repair of bone fractures, one or more orthopaedic devices, each orthopaedic device having an orthopaedic plate and a bone screw, may stabilize adjacent bone fragments relative to one another during the healing process. Similarly, during spinal fusion surgery one or more orthopaedic devices that span adjacent vertebrae, along with an intervening bone graft, may stabilize the spine during the healing process. Typically, the repair or surgery involves holding each orthopaedic plate in a desired location on the adjacent bone fragments or vertebrae and, then, using a drill or an awl making a hole for each screw. In some cases, a tap later creates threads within each hole for the subsequent placement of each screw. In other cases, a self-tapping screw creates the threads.

Conventional orthopaedic devices have an orthopaedic plate with a flat or curved profile and various arrangements and alignments of screw holes. The profile and the arrangement and alignment of screw holes depends on the specific application of the orthopaedic plate. In some cases, depending on an angle of the orthopaedic plate to an anterior body wall, a person applying the orthopaedic plate (e.g., a surgeon, a surgeon's assistant) may prefer to angulate one or more screws that fit within the screw holes for trajectory.

Disadvantages result because, during application of the orthopaedic plate and placement of the screws that fix the orthopaedic plate to the bones or vertebrae, surrounding soft tissue (e.g. muscle, tendon, ligaments, blood vessels) gets caught and winds around the drill or screws as the screws advance through the screw holes of the orthopaedic plate. A person applying the orthopaedic plate may use a tissue retractor to hold the soft tissue away from the orthopaedic plate, drill and screws. However, the use of a tissue retractor is not conducive to a minimally invasive approach, which is intended to cause less injury to the surrounding tissue. Yet additional disadvantages result because use of the tissue retractor is often difficult and unfeasible. Moreover, additional disadvantages result because the person applying the orthopaedic plate may not be able to angulate one or more of the screws that fit within the screw holes because the screws have a fixed trajectory relative to the orthopaedic plate.

A need exists for improved technology, including technology that may address one or more of the above described disadvantages of conventional orthopaedic devices. For example, a need exists for an orthopaedic device with screws that have a variable trajectory relative to the orthopaedic plate.

SUMMARY

According to one embodiment, an orthopaedic device for repairing a portion of a body, the orthopaedic device comprises an orthopaedic plate, a tissue protector, and a rotating member. The orthopaedic plate is configured to attach to at least one bone. The tissue protector is attached to the orthopaedic plate and configured to at least partially detach from the orthopaedic plate after a force is applied to the tissue protector. The rotating member is configured to connect the tissue protector to the orthopaedic plate while allowing the tissue protector to rotate relative to the orthopaedic plate.

BRIEF DESCRIPTION OF THE DRAWINGS

These and other features, aspects and advantages of the disclosed embodiments will become apparent from the following description, appended claims and the accompanying exemplary embodiments shown in the drawings, which are briefly described below.

FIG. 2C is a side view of the orthopaedic device of FIG. 2A where fasteners have been fully inserted into the spine.

FIG. 2D is a side view of the orthopaedic device of FIG. 2A where fasteners have been fully inserted into the spine and the tissue protectors are detached from the orthopaedic plate.

FIG. 3A is a side elevated view of a portion of an orthopaedic device having an orthopaedic plate with a flat profile and semi-cylindrically shaped tissue protectors.

FIG. 3B is a top view of an orthopaedic device having an orthopaedic plate with a flat profile and semi-cylindrically shaped tissue protectors.

FIG. 3C is a cross section of the orthopaedic device of FIG. 3B taken along line 3C-3C.

FIG. 3D is a side view of the orthopaedic device of FIG. 3B.

FIG. 3E is a front view of the orthopaedic device of FIG. 3B.

FIG. 6A is a side elevated view of a portion of an orthopaedic device having an orthopedic plate with a curved profile and semi-cylindrically shaped tissue protectors.

FIG. 6B is a top view of an orthopaedic device having an orthopedic plate with a curved profile and semi-cylindrically shaped tissue protectors.

FIG. 6C is a cross section of the orthopaedic device of FIG. 6B taken along line 6C-6C.

FIG. 6D is a side view of the orthopaedic device of FIG. 6B.

FIG. 6E is a front view of the orthopaedic device of FIG. 6B.

FIG. 7A is a side elevated view of an orthopaedic device having an orthopaedic plate with a curved profile and semi-cylindrically shaped tissue protectors.

FIG. 7B is a side elevated view of the orthopaedic device of FIG. 7A with fasteners being inserted into openings of the orthopaedic plate.

FIG. 10A is a side perspective view of an orthopaedic device having an orthopaedic plate with a curved profile, a semi-cylindrically shaped tissue protector connected to the orthopaedic plate, a semi-cylindrically shaped tissue protector substantially detached from the orthopaedic plate and a connecting band.

FIG. 10B is a top view of FIG. 10A.

FIG. 10C is a cross section of the orthopaedic device of FIG. 10B taken along line 10C-10C.

FIG. 10D is a cross section of the orthopaedic device of FIG. 10B taken along line 10D-10D.

DETAILED DESCRIPTION

Figure 1:
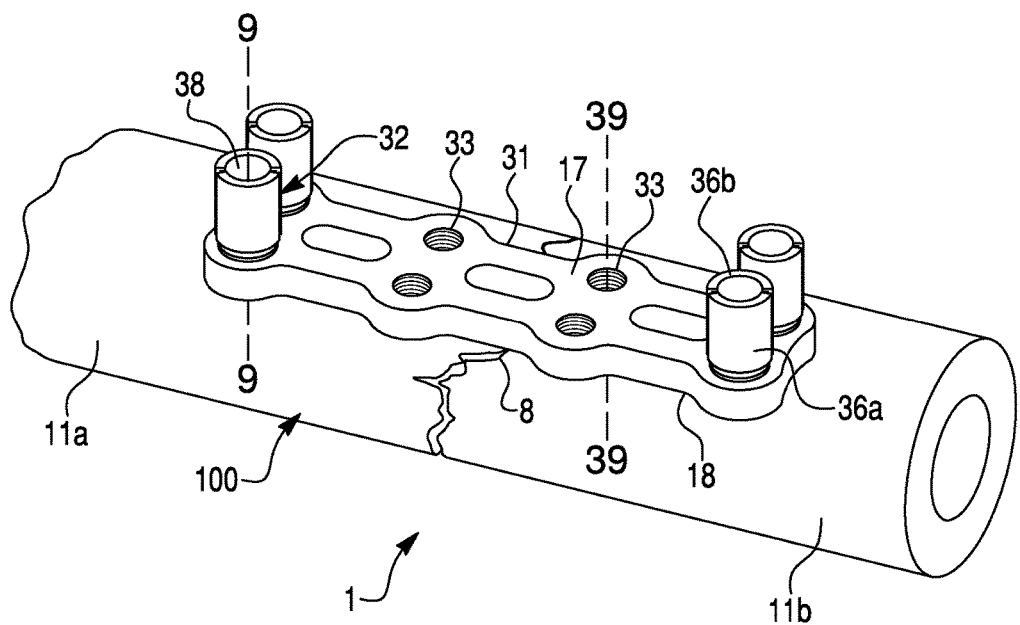
FIG. 1 is a top elevated view of an orthopaedic device having an orthopaedic plate and tissue protectors where the orthopaedic device is attached to a fractured bone.
Figure 2A:
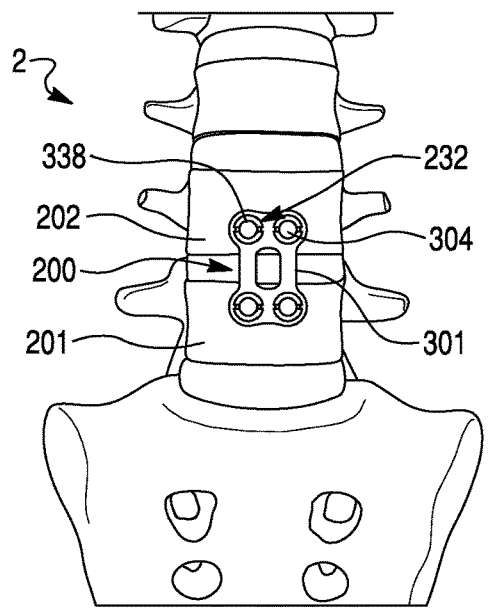
FIG. 2A is a front view of an orthopaedic device having an orthopaedic plate and semi-cylindrically shaped tissue protectors where the orthopaedic device is attached to the spine.
Figure 2B:
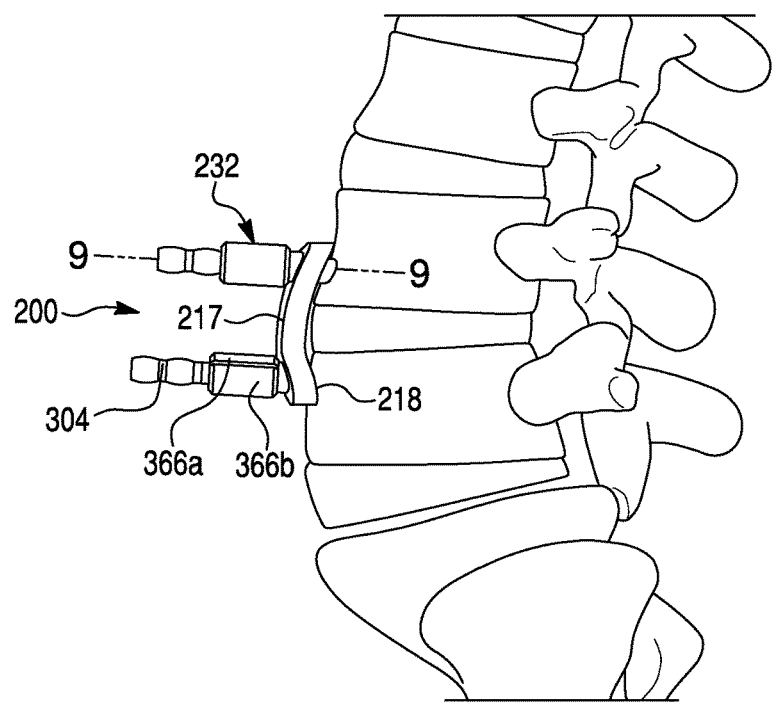
FIG. 2B is a side view of the orthopaedic device of FIG. 2A.

Presently preferred embodiments are illustrated in the drawings. An effort has been made to use the same or like reference numbers throughout the drawings to refer to the same or like parts. The disclosure relates to an orthopaedic device for repairing parts of the body. The orthopaedic device attaches to a patient's body using minimally invasive procedures so as to protect the patient's soft tissue.

FIGS. 1-20 illustrate embodiments of an orthopaedic device 100, 200, 300, 400, 600, 700, 800, 900, 1000, 1100, 2000, 3000. An orthopaedic device 100, 200, 300, 400, 600, 700, 800, 900, 1000, 1100, 2000, 3000 may be used to facilitate repair of a portion of a patient's body. The orthopaedic device 100, 200, 300, 400, 600, 700, 800, 900, 1000, 1100, 2000, 3000 may include an orthopaedic plate 31, 131, 301, 1101, 2031, 3031 and a tissue protector 32, 232, 332, 632, 732, 832, 932, 1032, 1132, 2032.

The orthopaedic plate 31, 131, 301, 1101, 2031, 3031 is configured to be attached to at least one bone. For example, the orthopaedic plate 31, 131, 301, 1101 (FIG. 1) may be attached to a first portion 11a and a second portion 11b of a bone segment 1 to facilitate repair of a fracture 8 in the bone segment 1. Alternatively, the orthopaedic plate 31, 131, 301, 1101 (FIGS. 2A-2D) may attach to adjacent vertebrae 201, 202 of a vertebral column 2. The bone may be planar (e.g. flat bones, such as the pelvis, skull, scapula), tubular or other shapes. The aforementioned examples are not intended to be limiting.

The orthopaedic plate 31, 131, 301, 1101, 2031, 3031 may comprise one or more openings (or holes) 33, 303, 333, 403, 2033, 3033 that extend through the orthopaedic plate 31, 131, 301, 1101, 2031, 3031. For example, the orthopaedic plate may have one hole, two holes (FIG. 12), four holes (FIGS. 2A-7D, 10A-10D, 13, 16A, 18A and 19A), six holes (FIG. 1), or some other configuration.

Each hole 33, 303, 333, 403, 2033, 3033 is configured to receive a fastener 304 (FIGS. 2A-2B, 7A-7C, 8A-8B, 9, 10A-10D and 11). The fastener 304 extends through a hole to attach the orthopaedic plate to a part of the body, such as a bone. A tissue protector 32, 232, 332, 632, 732, 832, 932, 1032, 1132, 2032 may be configured to receive the fastener 304. The fastener 304 may be any suitable fastener (e.g. a screw). The fastener may have one thread pitch for a first portion 1256 of the fastener 304 that fits within a part of the body and a different thread pitch for a second portion 1257 of the fastener 304 that fits within the orthopaedic plate 31, 131, 301, 1101 (FIGS. 8A, 9, 10A, 10D and 11). For example, the first portion 1256 of the fastener 304 may have a courser thread than the second portion 1257 of the fastener 304 or the first portion 1256 may have a taper that expands toward the screw head so the threads of the first portion 1256 may cut through a thinned section 371 of the tissue protector 32, 232, 332, 632, 732, 832, 932. In the former example, the differences in thread pitch may provide a lag effect to translate and press the orthopaedic plate 31, 131, 301, 1101 against the part of the body. In contrast, when the thread pitch is the same for the first and second portions 1256, 1257 of the fastener 304, the orthopaedic plate 31, 131, 301, 1101 is not pressed against the part of the body as much as when the thread pitches for the first and second portions 1256, 1257 are different. The first and second portions 1256, 1257 of the fastener 304 may be cylindrically-shaped (FIGS. 7B-7C, 8A-8B, 9, 10A, 10C-10D and 11), conically-shaped or any other suitable shape. Alternatively, one of the first and second portions 1256, 1257 of the fastener 304 may be cylindrically-shaped and the other of the first and second portions 1256, 1257 of the fastener 304 may be conically-shaped. The conically-shaped fastener helps assist in detaching (or shearing off) the tissue protector from the orthopaedic plate.

The holes 33, 303, 333, 403, 2033, 3033 of the orthopaedic plate 31, 131, 301, 1101, 2031, 3031 may be positioned anywhere along the orthopaedic plate. When the orthopaedic plate includes holes 403 at just one end (FIG. 12), the orthopaedic plate 1101 may be used as a buttress device such that the orthopaedic plate 1101 may be secured at one end to a bone and the rest of the orthopaedic plate 1101 may span over, but is not secured to, another bone to buttress the bone. For example, the buttressing part of an anteriorly placed spinal plate may be positioned to prevent an adjacent structural bone graft from dislodging anteriorly or to the side. When the orthopaedic plate has multiple holes, the rigidity between the orthopaedic plate 31, 131, 301, 1101, 2031, 3031 (FIGS. 1-20) and the part(s) of the body to which the orthopaedic plate attach(es) increase(s) as the number of holes through which fasteners 304 are fastened increases.

When the orthopaedic plate 31, 131, 301, 1101, 2031, 3031 has multiple openings, not all of the holes need to be securely attached to a tissue protector. For example, when the orthopedic plate 31 has six holes (FIG. 1), only four of the holes may each be securely attached to a tissue protector or when the orthopaedic plate has four holes (FIGS. 13, 16A, 18A and 19A) only one of the holes may be securely attached to a tissue protector. To increase the protection to a patient's soft tissue, preferably at least the holes at the outer corners of the orthopaedic plate (e.g. the four outer holes at the outer corners of the six hole orthopaedic plate 31) each include a tissue protector.

The relative trajectory of the openings 33, 303, 333, 403 (FIGS. 1, 2D, 3D and 10C) may be parallel, converging or diverging such that the opening 33, 303, 333, 403, 2033, 3033 may one of extend parallel to, diverge from and converge from a longitudinal axis 39-39, 309-309, 539-539, 2039-2039, 3039-3039 (FIGS. 1, 2D, 3D, 10C, 13, 15A-15B, 16C, 18C and 19C) of the hole 33, 303, 333, 403, 2033, 3033. The trajectory depends on the surface of the body on which the orthopaedic plate 31, 131, 301, 1101, 2031, 3031 is intended to attach.

The openings 33, 303, 333, 403, 2033, 3033 may be any suitable size and may comprise threads that mate with the fasteners. For example, the diameter of the holes 33, 303, 333, 403, 2033, 3033 may range from 3.5 mm to 6 mm. The holes 33, 303, 333, 403, 2033, 3033 may be threaded by any suitable threading mechanism. For example, the holes 33, 303, 333, 403, 2033, 3033 may be threaded by a fastener 304 (e.g. a self-threading fastener) or by a threading element (e.g. a tap). Alternatively, the holes 33, 303, 333, 403, 2033, 3033 may not be threaded.

The orthopaedic plate 131 may comprise a tab 80 (FIGS. 5B-5C) extending from a bottom surface 412 of the orthopaedic plate 131 and configured to insert into one of an opening in the bone and an opening between adjacent bones. The orthopaedic plate 131 may comprise one or more tabs 80. The bottom surface 412 of the orthopaedic plate 131 is opposite to the top surface 413 of the orthopaedic plate 131 and abuts a bone when the orthopaedic plate 131 contacts a bone. The tab 80 decreases the amount of force that each fastener 304 fastened to the orthopaedic plate 131 and the body must share. Preferably, the tab 80 is used to connect to vertebrae where the tab 80 inserts into an intervertebral space. The tab 80 is generally a 1 mm to 3 mm projection that is parallel to the vertebral bony end plate and the tab 80 may be 3 mm wide up the width of the orthopaedic plate.

The orthopaedic plate 31, 131, 1101, 2031, 3031 may have a flat profile (FIGS. 1 and 3A-5D), a curved profile (FIGS. 2A-2D, 6A-11 and 13-20) or other profile suitable for the intended use. Orthopaedic plates with a flat profile can be placed on a portion of the body having a flat profile. Orthopaedic plates with a curved profile can be placed on a portion of the body having a curved profile. Regardless of the profile of the orthopaedic plate 31, 131, 301, 1101, 2031, 3031 the orthopaedic plate 31, 131, 301, 1101, 2031, 3031 may be any suitable width, length and height and may comprise any suitable material. For example, the orthopaedic plate may be 8 mm to 20 mm wide, 25 mm to 150 mm long and 2 mm to 6 mm high. The orthopaedic plate 31, 131, 301, 1101, 2031, 3031 can be formed, for example, of titanium, stainless steel, cobalt-chrome alloy, carbon fiber, PEEK (Polyether ether ketone) or a composite of these materials.

The tissue protector 32, 232, 332, 632, 732, 832, 932, 1032, 1132, 2032 securely attaches (e.g. strongly fits) to the orthopaedic plate 31, 131, 301, 1101, 2031, 3031 and is configured to at least partially detach from the orthopaedic plate 31, 131, 301, 1101, 2031, 3031 after a force, such as a substantial force, is applied to the tissue protector 32, 232, 332, 632, 732, 832, 932, 1032, 1132, 2032. The secure attachment may be any suitable attachment. For example, the secure attachment may be that the tissue protector 32, 232, 332, 632, 732, 832, 932, 1032, 1132, 2032 integrally attaches to the orthopaedic plate 31, 131, 301, 1101, 2031, 3031. The orthopaedic plate 31, 131, 301, 1101, 2301, 3031 and the tissue protector 32, 232, 332, 632, 732, 832, 932, 1032, 1132, 2032 can be integrally attached via any suitable mechanism. For example, the orthopaedic plate 31, 131, 301, 1101, 2031, 3031 and the tissue protector 32, 232, 332, 632, 732, 832, 932, 1032, 1132, 2032 could be machined from a single piece of metal stock and/or separate pieces of metal stock. If the orthopaedic plate 31, 131, 301, 1101, 2301, 3031 and the tissue protector 32, 232, 332, 632, 732, 832, 932, 1032, 1132, 2032 are made from separate pieces of metal stock, then they may be welded or shrink fit together at an interface or just below the top surface 17, 217, 317, 1117, 2117, 3117 (FIGS. 1, 2B, 4A, 12-13 and 16) of the orthopaedic plate 31, 131, 301, 1101, 2031, 3031. The top surface 17, 217, 317, 1117, 2117, 3117 of the orthopaedic plate 31, 131, 301, 1101, 2031, 3031 is the surface of the orthopaedic plate from which fasteners are first received in the orthopaedic plate 31, 131, 301, 1101, 2031, 3031 and is distal from a bottom surface 18, 218, 318, 2118, 3118 (FIGS. 1, 2B, 4A, 13 and 16) of the orthopaedic plate 31, 131, 301, 1101, 2031, 3031 that is configured to abut the part of the body. Welding may be done by any suitable method of welding (e.g. laser or electro-welding). The tissue protector may also be referred to as a split bushing, blade or sleeve.

There may be one or more tissue protectors 32, 232, 332, 632, 732, 832, 932, 1032, 1132, 2031 attached to the orthopaedic plate 31, 131, 301, 1101, 2031, 3031. For example, four tissue protectors may attach to the orthopaedic plate (FIGS. 1, 3A-3B, 4A-4B, 5A, 6A-6B). Alternatively, two tissue protectors 1132 (FIGS. 10A and 11) may attach to the orthopaedic plate 1101 or one tissue protector 2032 (FIGS. 13-20) may attach to the orthopaedic plate 2031, 3031. The number of tissue protectors may equal the number of openings in the orthopaedic plate (FIGS. 3A-3B, 4A-4B, 5A, 6A-6B, 12) or the number of tissue protectors may be less than the number of openings in the orthopaedic plate (FIGS. 1, 10A and 13-20).

The tissue protector 32, 232, 332, 632, 732, 832, 932, 1032, 1132, 2032 is configured to prevent surrounding tissue from interfering with fixation of the fastener 304 to the orthopaedic plate 31, 131, 301, 1101, 2031, 3031 or at least reduce negative effects. The tissue protector 32, 232, 332, 632, 732, 832, 932, 1032, 1132, 2032 may prevent the top of the fastener 304 and, if the fastener 304 is threaded, its threads from injuring the surrounding tissue, or at least reduce negative effects. Additionally, the tissue protector 32, 232, 332, 632, 732, 832, 932, 1032, 1132, 2032 may keep the tissue from wrapping around the fastener 304 when the fastener 304 advances through the opening 33, 303, 333, 403, 2033, 3033 of the orthopaedic plate 31, 131, 301, 1101, 2031, 3031 or at least reduce the wrapping of the tissue.

The tissue protector 32, 232, 332, 632, 732, 832, 932, 1032, 1132, 2032 may comprise any suitable material. For example, the tissue protector 32, 232, 332, 632, 732, 832, 932, 1032, 1132, 2032 may comprise titanium, stainless steel, cobalt-chrome alloy, carbon fiber, PEEK (Polyether ether ketone) or a composite of these materials.

The tissue protector 32, 232, 332, 632, 732, 832, 932, 1032, 1132, 2032 includes an opening 38, 58, 338, 408, 508, 1208, 2038 (FIGS. 1, 2A, 3B-3C, 5A, 6A, 7A, 10A, 13 and 16C) that extends through the tissue protector 32, 232, 332, 632, 732, 832, 932, 1032, 1132, 2032 along a longitudinal axis 9-9, 409-409, 509-509, 1209-1209, 2009-2009 (FIGS. 1, 2B, 3C, 5B, 6A, 7A, 10D and 13) of the tissue protector. The opening 38, 58, 338, 408, 508, 1208, 2038 extends from the bottom most portion of the tissue protector 32, 232, 332, 632, 732, 832, 932, 1032, 1132, 2032 to the top most portion of the tissue protector 32, 232, 332, 632, 732, 832, 932, 1032, 1132, 2032. The opening 38, 58, 338, 408, 508, 1208, 2038 is sized to allow a fastener 304 to be disposed within the tissue protector 32, 232, 332, 632, 732, 832, 932, 1032, 1132, 2032. The opening 38, 58, 338, 408, 508, 1208, 2038 may or may not be threaded. If the opening 38, 58, 338, 408, 508, 1208, 2038 is threaded, it may be threaded by a fastener 304 (e.g. a self-threading fastener) or by a threading element (e.g. a tap). The threads could be fine or course.

The tissue protector 32, 232, 332, 632, 732, 832, 932, 1032, 1132, 2032 may include a thinned section or region 371 (FIGS. 4A, 6A, 8A-8B, 9, 10, 12D, 13 and 17) at a junction 372 (e.g. portion) (FIGS. 6A, 8A, 9, 10) of the tissue protector proximate to the orthopaedic plate. The junction may be between the orthopaedic plate 31, 131, 301, 1101, 2031, 3031 and the tissue protector 32, 232, 332, 632, 732, 832, 932, 1032, 1132, 2032. The thinned section or region 371 may also be referred to as a circumferential notch. The thinned section 371 is positioned adjacent to the orthopaedic plate 31, 131, 301, 1101, 2031, 3031.

Figure 4B:
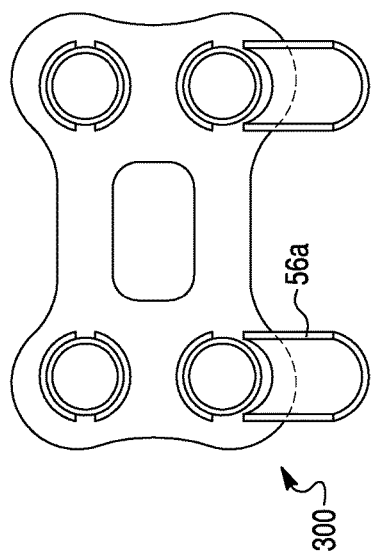
FIG. 4B is a top view of the orthopaedic device of FIG. 4A.
Figure 4D:
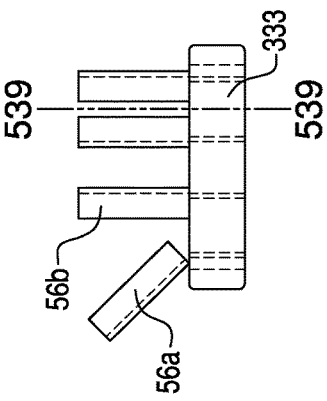
FIG. 4D is a front view of the orthopaedic device of FIG. 4A.
Figure 4A:
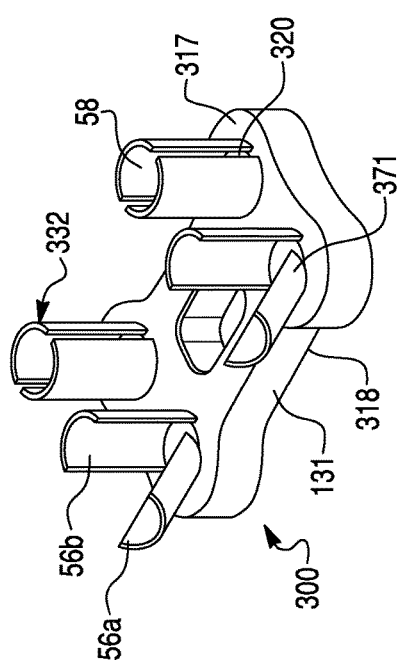
FIG. 4A is a side elevated view of the orthopaedic device of FIG. 3B where some of the tissue protectors are in the process of detaching from the orthopaedic plate.
Figure 4C:
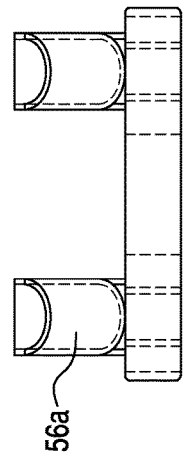
FIG. 4C is a side view of the orthopaedic device of FIG. 4A.
Figure 5A:
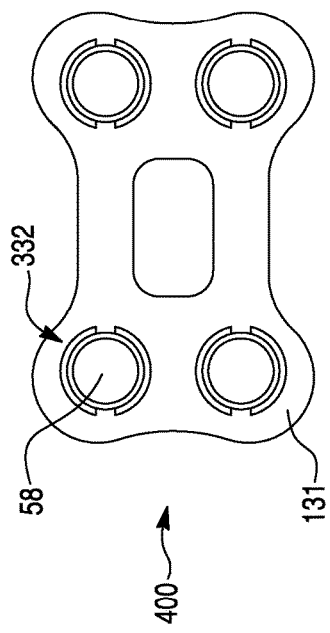
FIG. 5A is a top view of an orthopaedic device having an orthopaedic plate with a flat profile and semi-cylindrically shaped tissue protectors.
Figure 5C:
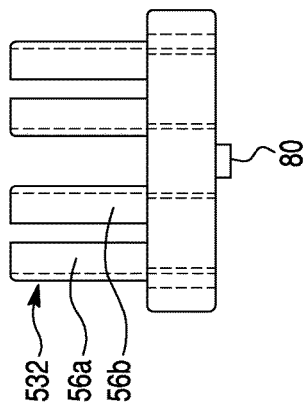
FIG. 5C is a front view of the orthopaedic device of FIG. 5A.
Figure 5B:
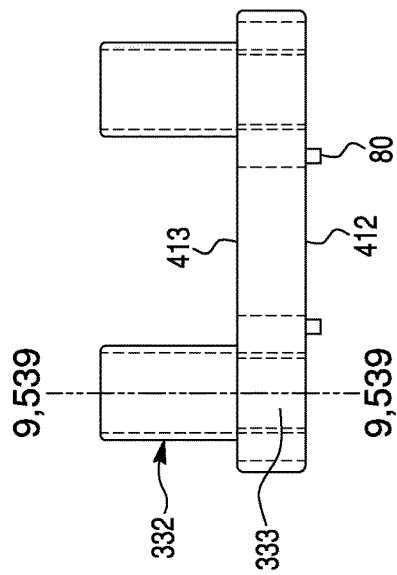
FIG. 5B is a side view of the orthopaedic device of FIG. 5A.

The thinned section 371 one of extends continuously and discontinuously around a circumference of the tissue protector 32, 232, 332, 632, 732, 832, 932, 1032, 1132, 2032. For example, as shown in FIG. 6A the thinned section 371 may extend around the entire circumference of the tissue protector 632. Alternatively, as shown in FIGS. 3A and 4A the thinned section 371 may be at one or more locations along the circumference of the tissue protector 332.

Figure 7C:
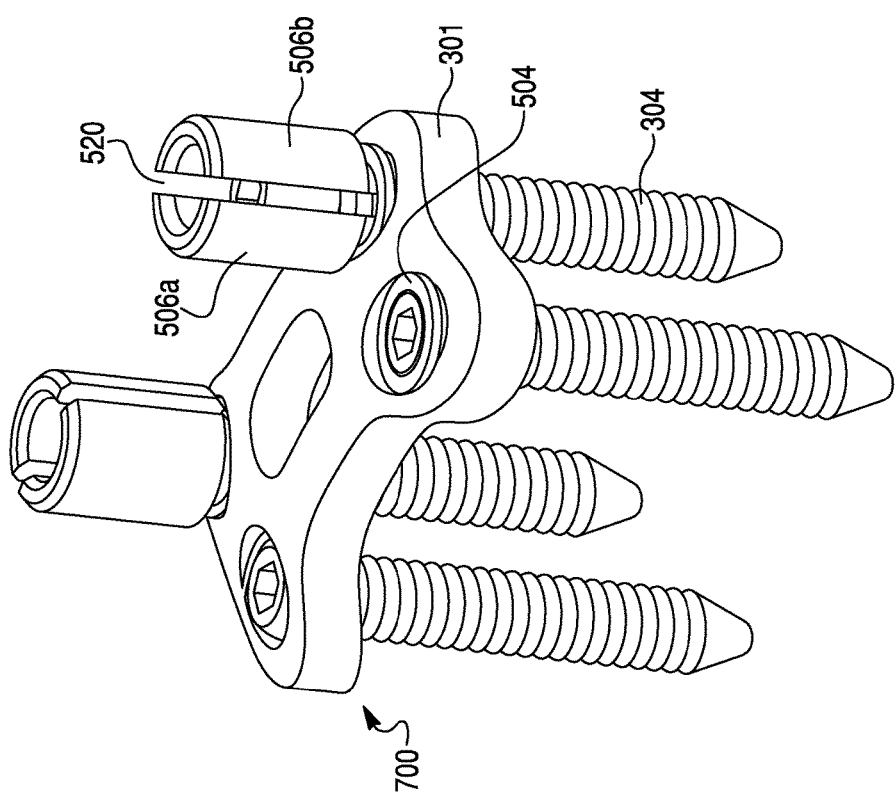
FIG. 7C is a side elevated view of the orthopaedic device of FIG. 7A with fasteners fully inserted into openings of the orthopaedic plate.
Figure 8A:
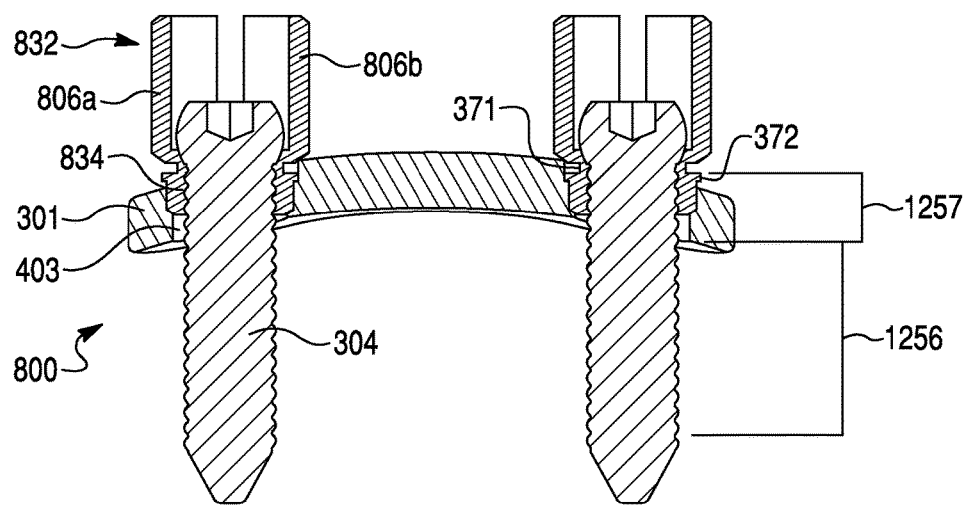
FIG. 8A is a cross-section of an orthopaedic device having an orthopaedic plate with a curved profile and semi-cylindrically shaped tissue protectors.
Figure 8B:
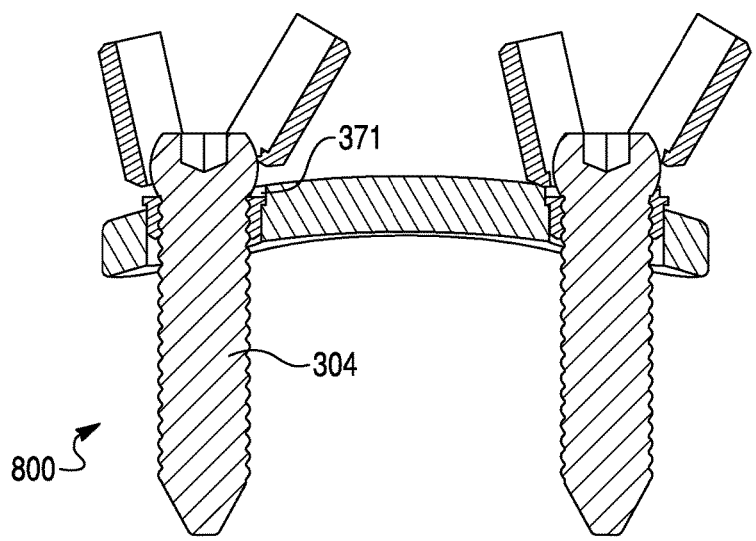
FIG. 8B is a cross-section of the orthopaedic device of FIG. 8A where the semi-cylindrical tissue protectors are in the process of detaching from the orthopaedic plate.
Figure 11:
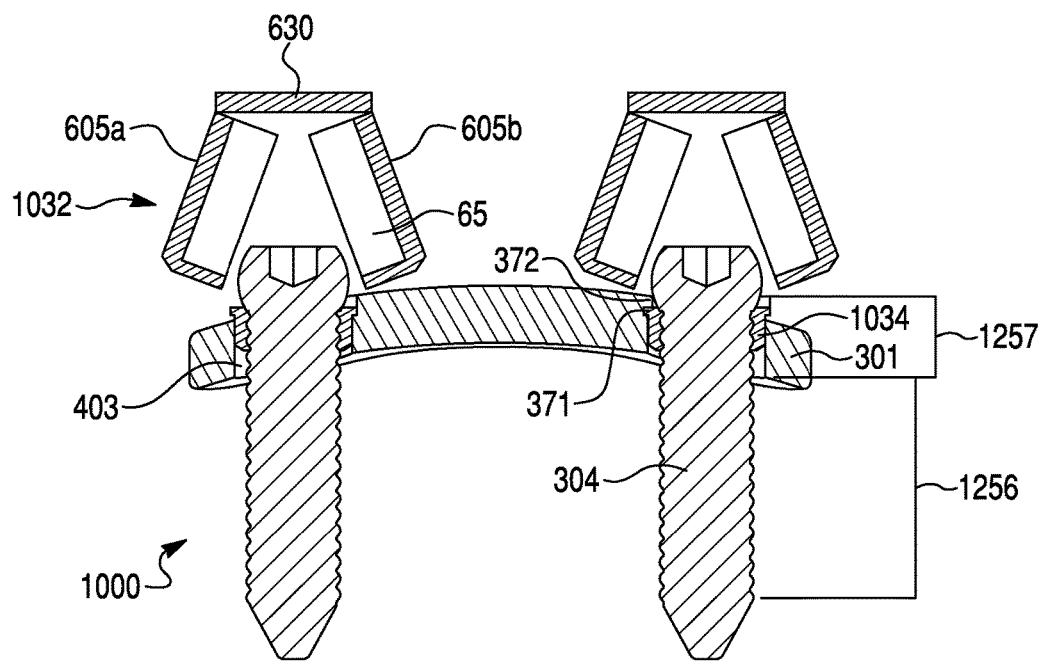
FIG. 11 is a cross-section of an orthopaedic device having an orthopaedic plate with a curved profile and semi-cylindrically shaped tissue protectors which include a connecting band and are in the process of detaching from the orthopaedic plate.
Figure 12:
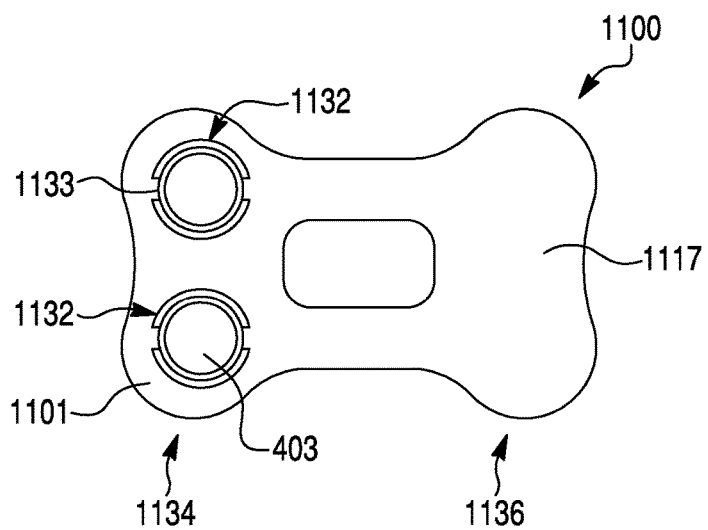
FIG. 12 is a top view of an orthopaedic device having an orthopaedic plate and tissue protectors.

The thinned section 371 is configured to cause the tissue protectors 32, 232, 332, 632, 732, 832, 932, 1032, 1132, 2032 to at least partially detach from the orthopaedic plate 31, 131, 301, 1101, 2031, 3031 when the force is applied to the thinned section 371. The thinned section 371 is able to cause the tissue protectors 32, 232, 332, 632, 732, 832, 932, 1032, 1132, 2032 to at least partially detach from the orthopaedic plate 31, 131, 301, 1101, 2031, 3031 when the force is applied to the thinned section 371 because the thinned section 371 has a thinner width than the remainder of the tissue protector 32, 232, 332, 632, 732, 832, 932, 1032, 1132, 2032 and/or a smaller outer diameter than the remainder of the tissue protector 32, 232, 332, 632, 732, 832, 932, 1032, 1132, 2032. The thinned section 371 causes substantially all or the entirety of each tissue protector 32, 232, 332, 632, 732, 832, 932, 1032, 1132, 2032 to detach from or shear off of the orthopaedic plate 31, 131, 301, 1101 when the suitable force is applied to the thinned section. FIGS. 7C, 8B and 11 show a tissue protector 532, 732, 932, 1032, 2032 when a substantial portion 66a, 504, 934, 1034 of the tissue protector 532, 732, 932, 1032, 2032 has detached from the orthopaedic plate 301. FIG. 2D shows a tissue protector 232 where all of the tissue protector 232 is detached from the orthopaedic plate 301 and FIG. 10A shows a tissue protector 1032 where one has not detached while the other has substantially detached from the orthopaedic plate 301 such that only a portion 1220 of the substantially detached tissue protector 1032 remains. The fastener 304 may be fully advanced in the orthopaedic plate 31, 131, 231, 301, 2031, 3031 and the tissue protector 32, 232, 332, 432, 532, 632, 732, 832, 932, 1032, 2032 may still be in the orthopaedic plate, but when the fastener 304 is fully tightened a suitable force is applied to the tissue protector 32, 232, 332, 432, 532, 632, 732, 832, 932, 1032, 2032, 3032 such that the tissue protector 32, 232, 332, 432, 532, 632, 732, 832, 932, 1032, 2032, 3032 detaches from the orthopaedic plate.

The tissue protector 32, 232, 332, 432, 532, 632, 732, 832, 932, 1032, 2032, 3032 may include a first leaf 36a, 56a, 366a, 406a, 506a, 505a, 605a, 806a, 2036a and a second leaf 36b, 56b, 366b, 406b, 506b, 505b, 605b, 806b, 2036b (FIGS. 1, 2B, 3A, 4A, 5C, 6A, 7A, 8A, 9, 10A, 10D, 11, 13 and 16C). The leaves 36a, 36b, 56a, 56b, 366a, 366b, 406a, 406b, 506a, 506b, 505a, 505b, 605a, 605b, 806a, 806b, 2036a, 2036b may connect to the orthopaedic plate 31, 131, 301, 1101, 2031, 3031. Although the figures show each tissue protector 32, 232, 332, 632, 732, 832, 932, 1032, 1132, 2032 having two leaves 36a, 36b, 56a, 56b, 366a, 366b, 406a, 406b, 506a, 506b, 505a, 505b, 605a, 605b, 806a, 806b, 2036a, 2036b each tissue protector 32, 232, 332, 632, 732, 832, 932, 1032, 2032 may have more than two leaves.

The first leaf 36a, 56a, 366a, 406a, 506a, 505a, 605a, 806a, 2036a and the second leaf 36b, 56b, 366b, 406b, 506b, 505b, 806b, 2036b may extend from the thinned region 371 and are positioned farther from the orthopaedic plate 31, 131, 301, 1101, 2031 than the thinned region 371 is from the orthopaedic plate 31, 131, 301, 1101, 2031. The positioning of the leaves 36a, 36b, 56a, 56b, 366a, 366b, 406a, 406b, 506a, 506b, 505a, 505b, 605a, 605b, 806a, 806b, 2036a, 2036b with respect to the thinned region 371 is such that the thinned region 371 separates the leaves 36a, 36b, 56a, 56b, 366a, 366b, 406a, 406b, 506a, 506b, 505a, 505b, 605a, 605b, 806a, 806b, 2036a, 2036b from the orthopaedic plate 31, 131, 301, 1101, 2031, 3031.

Figure 13:
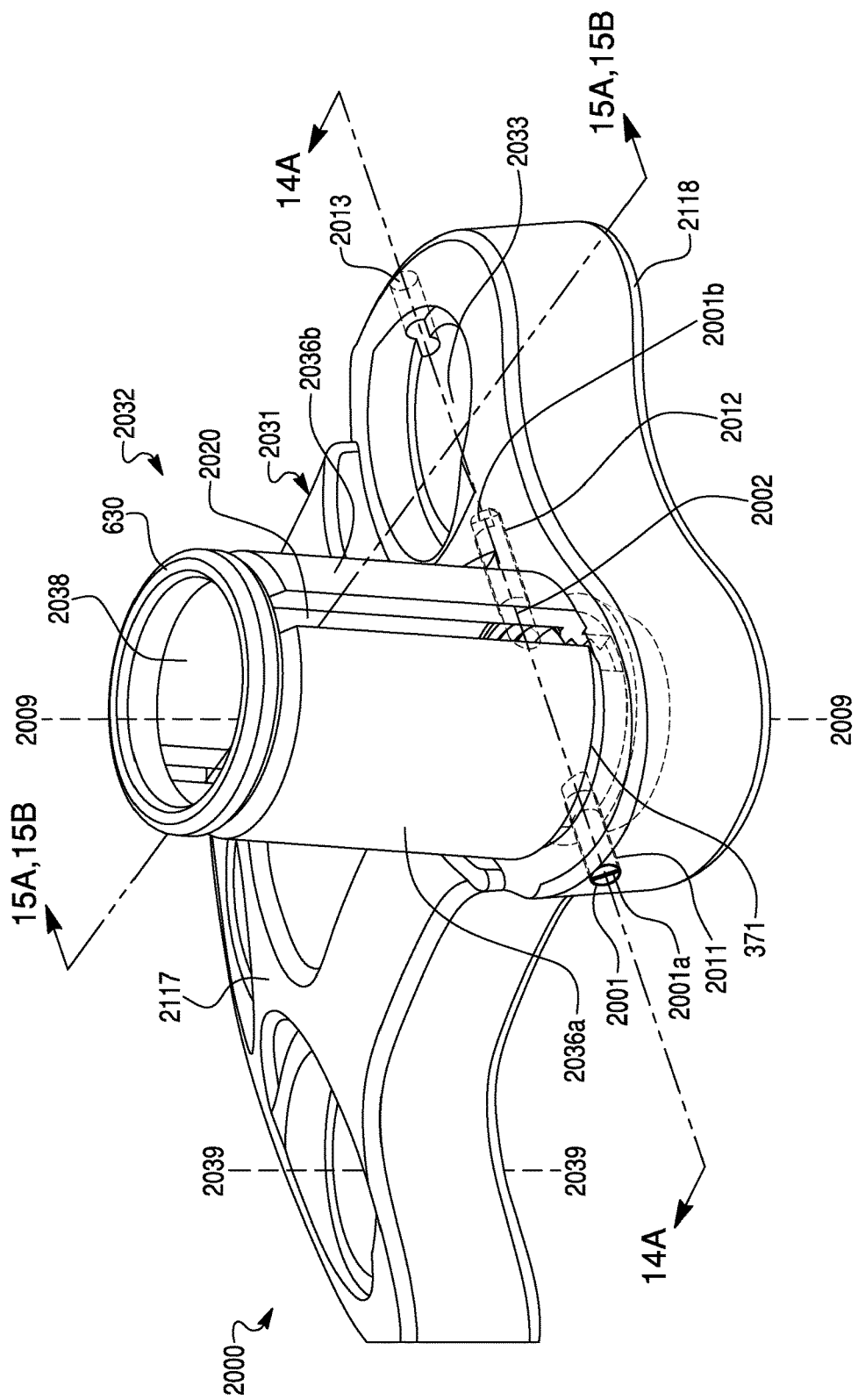
FIG. 13 is a side elevated view of an orthopaedic device having an orthopaedic plate, a tissue protector and a rotating member.

The first leaf 36a, 56a, 366a, 406a, 506a, 505a, 605a, 806a, 2036a may connect to the second leaf 36b, 56b, 366b, 406b, 506b, 505b, 605b, 806b, 2036b at the thinned region 371 when the thinned region 371 extends continuously around the circumference of the tissue protector (FIG. 6A) or the first leaf 36a, 56a, 366a, 406a, 506a, 505a, 605a, 806a, 2036a may be separate from the second leaf 36b, 56b, 366b, 406b, 506b, 505b, 605b, 806b, 2036b when the thinned region 371 extends discontinuously around the circumference of the tissue protector, such that the first and second leaf do not connect to each other (FIGS. 3A, 4A and 13). When the leaves connect to one another the leaves are stronger, such that the leaves will not detach from the orthopaedic plate until a force is applied (e.g. a substantial/suitable force is applied). In other words, the leaves will not detach from the orthopaedic plate inadvertently (e.g. prior to the fasteners being fully advanced into the orthopaedic plate) When the force is applied to each leaf, the leaf detaches from the orthopaedic plate. At least a portion of the first leaf 36a, 56a, 366a, 406a, 506a, 505a, 605a, 806a, 2036a may be disconnected from a portion of the second leaf 36a, 56a, 366a, 406a, 506a, 505a, 605a, 806a, 2036b Alternatively, all of the first leaf may connect to all of the second leaf.

The leaves 36a, 36b, 56a, 56b, 366a, 366b, 406a, 406b, 506a, 506b, 505a, 505b, 605a, 605b, 806a, 806b, 2036a, 2036b may have varying orientations (FIGS. 9 and 10) and widths for the space 320, 420, 520, 2020 (FIGS. 4A, 6A, 7C and 13) between adjacent leaves. The width for the space 320, 420, 520, 2020 between adjacent leaves may range from 0.5 mm to 5 mm, such as between 1 mm to 5 mm.

The tissue protector 32, 232, 332, 632, 732, 832, 2032 may comprise one of a substantially conical shape (FIG. 9), substantially cylindrical shape (FIGS. 1-8B, 10A, 10D, 11 and 13-20) or any other shape suitable for the intended use. The diameter of the tissue protectors 932 that are semi-conically shaped increase as the tissue protector 932 gets farther away from where the tissue protector 932 and the orthopaedic plate 301 integrally attach. The minimum and maximum diameter as well as the height of the semi-conically shaped tissue protectors 932 may vary. For example, the outer diameter of the tissue protectors 932 may range from 4 mm to 12 mm (for example, from 4 mm to 8 mm or 6 mm to 12 mm), the inner diameter may range from 4.5 mm to 11.5 mm (for example, from 4.5 mm to 7.5 mm or 6.5 mm to 11.5 mm) and the height may range from 4 mm to 15 mm. Each of the semi-conically shaped tissue protectors 932 allows for a slightly oversized screw head to fit into the opening of the tissue protector 932. The semi-cylindrically shaped tissue protectors 32, 232, 332, 632, 832, 1032, 2032 may have varying diameters and heights. For example, the diameter of the tissue protectors 32, 232, 332, 632, 832, 1032, 2032 may range from 4 mm to 12 mm (for example, from 4 mm to 8 mm or 6 mm to 12 mm), the inner diameter may range from 4.5 mm to 11.5 mm (for example, from 4.5 mm to 7.5 mm or 6.5 mm to 11.5 mm) and the height from 4 mm to 15 mm.

Figure 9:
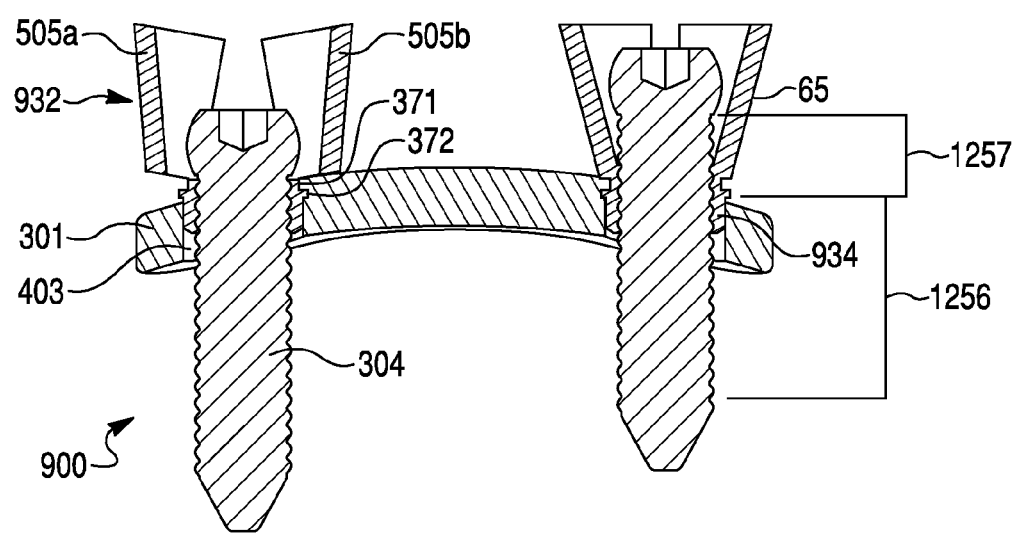
FIG. 9 is a cross-section of an orthopaedic device having an orthopaedic plate with a curved profile and semi-conically shaped tissue protectors, where one of the tissue protectors is in the process of detaching.

Although the semi-conically shaped tissue protectors 932 shown in FIG. 9, are integrally attached to a orthopaedic plate 301 with a curved profile, the semi-conically shaped tissue protectors 932 may integrally attach to an orthopaedic plate with a flat profile. Although, the figures show an orthopaedic plate with all semi-cylindrically shaped tissue protectors or all semi-conically shaped tissue protectors, an orthopaedic plate may have semi-cylindrically and semi-conically shaped tissue protectors. Although, the internal diameter of the tissue protectors 32, 232, 332, 632, 832, 932, 1032, 2032 is shown as being constant or substantially constant, the tissue protector may include a varying internal diameter.

The tissue protector 1032, 2032 may connect to a connecting band 630 (or collar or top plate) that connects the first leaf 605a, 2036a to the second leaf 605b, 2036b (FIGS. 10A, 11, 13-16C and 18A-20) at a position distal from where the tissue protector 1032, 2032 attaches to the orthopaedic plate 301, 2031, 3031. The tissue protector 1032, 2032 may be integrally connected to the collar 630 via any suitable mechanism. For example, the tissue protector 1032, 2032 and the collar 630 may be formed from the same sheet or the tissue protector 1032, 2032 and the collar 630 may be welded together. The connecting band 630 may connect the leaves 605a, 605b, 2036a, 2036b of the tissue protector 1032, 2032 together at the top portion of the tissue protector 1032, 2032. The top plate 630 may include an opening (not shown) through which the fastener 304 can fit.

The collar 630 is configured to hold the tissue protector 1032, 2032 together after the tissue protector 1032, 2032 is detached or sheared off from the orthopaedic plate 301, 2031, 3031. The collar 630 may also interact with a screw-driver when the fastener 304 is fastened (e.g. screwed) into the tissue protector 1032, 2032 so that, as the fastener 304 is tightened, the tissue protector shears off of the orthopaedic plate and the collar holds to the screw-driver so that the detached tissue protector may be easily retrieved. The top plate 630 prevents the leaves 605a, 605b, 2036a, 2036b from displacing from one another at the top end (e.g. end closest to where the fastener 304 enters the top plate 630) while the leaves 605a, 605b, 2036a, 2036b detach from the orthopaedic plate. The top plate 630 may have any suitable shape and may connect to any shaped tissue protector. For example, the top plate 630 may be ring-shaped (e.g. circular shaped) and the top plate 630 may connect to leaves of a semi-cylindrically shaped tissue protector (FIGS. 10A and 11) or semi-conically shaped tissue-protector.

A small elastomeric ring (e.g. an O-ring) may be placed at the outer bottom of one or more of the tissue protectors so that when the leaves are detached, there will be a barrier from potential sharp edges of the leaves at the detachment site. The elastomeric ring may be integrally attached to the tissue protector or separate from the tissue protector. Alternatively, a remaining portion 1220 (FIG. 10A) of the tissue protector 1032 may remain after a substantial portion of the leaves are detached so that there will be a barrier from potential sharp edges of the leaves at the detachment site. The remaining portion 1220 is attached to the orthopaedic plate 31, 131, 301, 1101, 2031, 3031. While the portion 1220 is only shown in the tissue protector 1032 of FIG. 10A, the portion may be part of any tissue protector. The remaining portion 1220 may be at a portion of the tissue protector proximate to the orthopaedic plate 31, 131, 301, 1101, 2031, 3031.

The orthopaedic device 2000, 3000 may also include a rotating member 2060, 3060 (FIGS. 14A, 14B and 17) that is configured to connect the tissue protector 2032 to the orthopaedic plate 2031, 3031 while allowing the tissue protector 2032 to rotate relative to the orthopaedic plate 2031, 3031. The rotating member 2060, 3060 may or may not be within the orthopaedic plate 2031, 3031. Preferably, the rotating member 2060, 3060 is within the orthopaedic plate 2031, 3031 so that the orthopaedic device is a low-profile device. The rotating member 2060, 3060 may help the tissue protector 2032 rotate relative to a longitudinal axis 2039-2039, 3039-3039 (FIGS. 13, 15A-15B, 16C, 18C and 19C) of the hole 2033, 3033 that extends through the orthopaedic plate 2031, 3031. The rotating member 2060, 3060 may allow the tissue protector to rotate in a single plane extending along the longitudinal axis (FIGS. 13-15B) or may allow infinite angulation of the tissue protector within a maximum of about 5-10 degrees from the longitudinal axis of the hole that extends through the orthopaedic plate (FIGS. 16A-20). When the tissue protector 2032 rotates, the angle of a fastener 304 relative to the orthopaedic plate 2031, 3031 that is within or that enters the tissue protector 2032 also rotates such that the fastener 304 has a variable trajectory relative to the orthopaedic plate 2031, 3031.

Figure 14A:
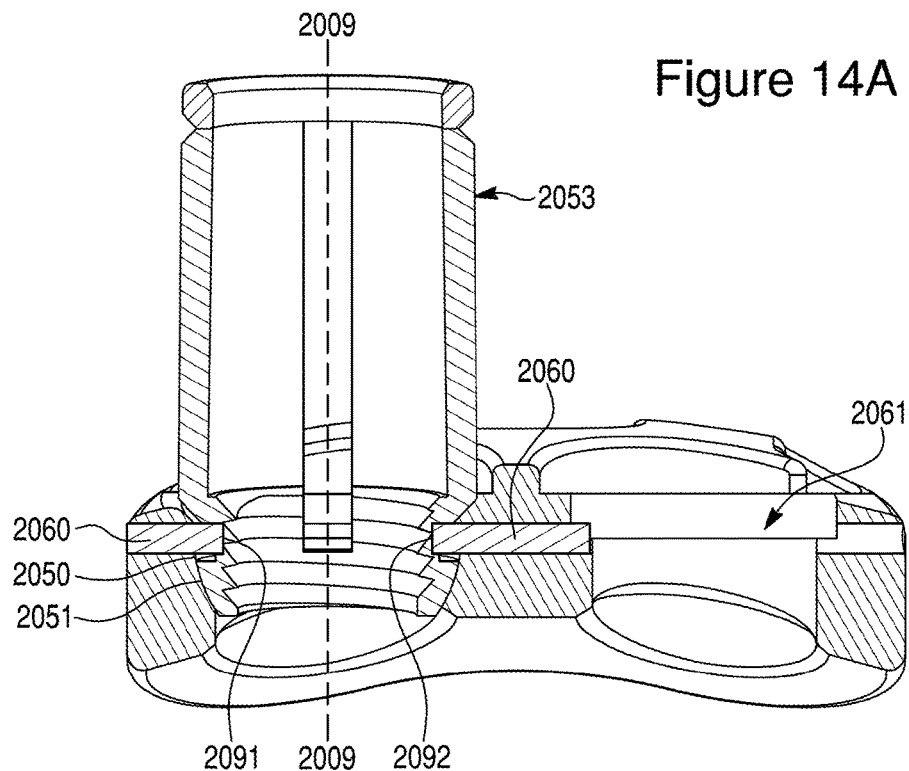
FIG. 14A is a cross-section of the orthopaedic device of FIG. 13 taken along line 14A-14A.
Figure 14B:
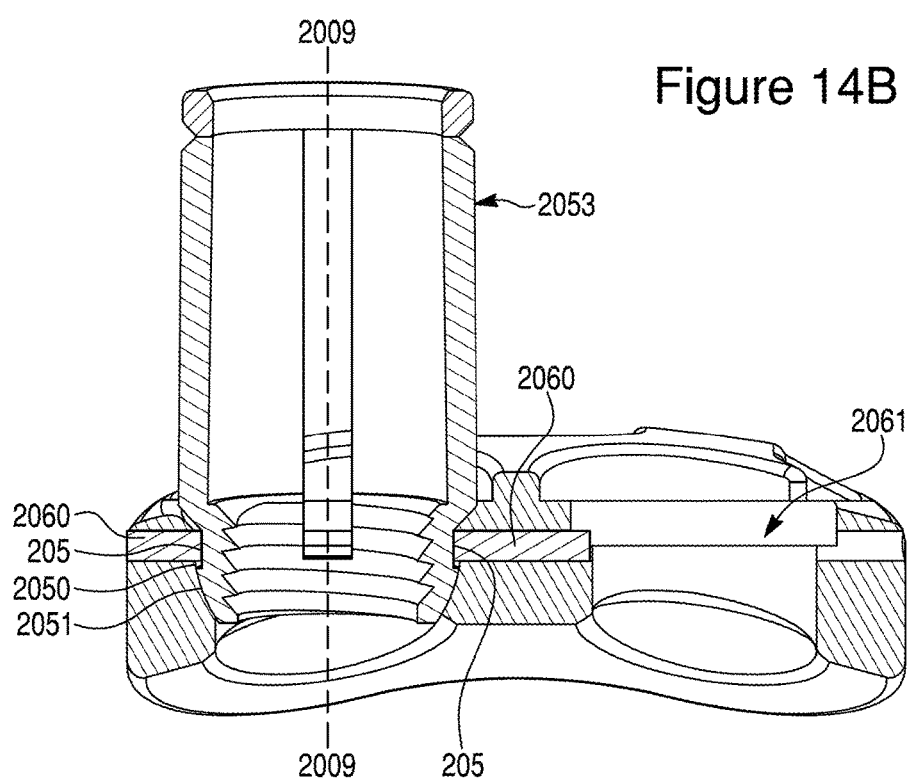
FIG. 14B is a cross-section of an orthopaedic device with a pin mechanism as a rotating member.
Figure 15A:
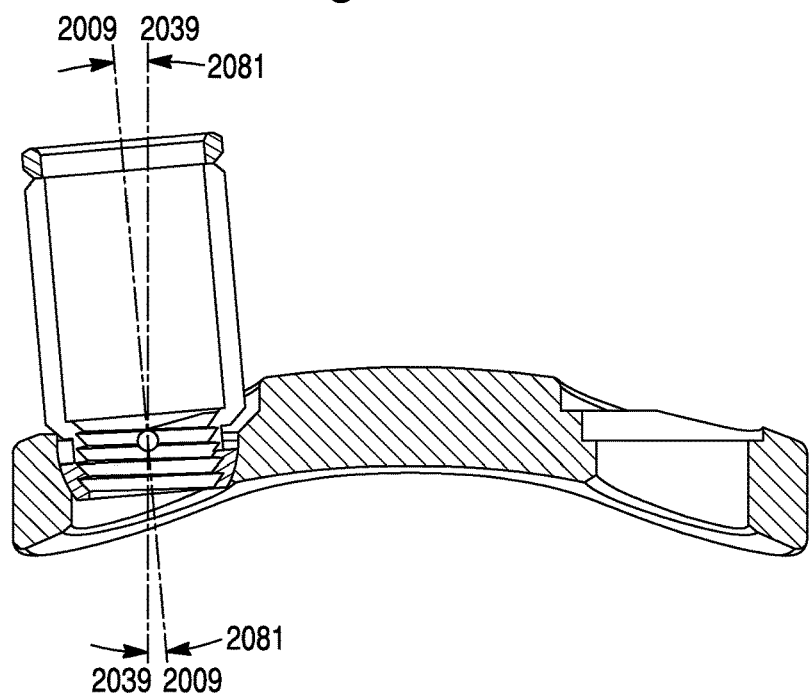
FIG. 15A is a cross-section of the orthopaedic device of FIG. 13 taken along line 15A-15A when the tissue protector has rotated about 5 degrees counterclockwise from a longitudinal axis that extends through the orthopaedic plate.
Figure 15B:
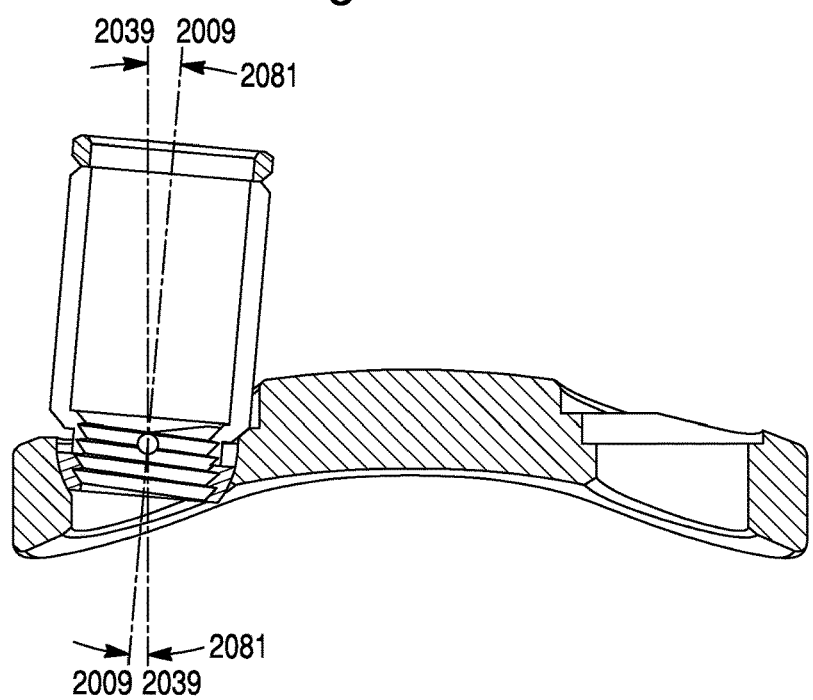
FIG. 15B is a cross-section of the orthopaedic device of FIG. 13 taken along line 15B-15B when the tissue protector has rotated about 5 degrees clockwise from a longitudinal axis that extends through the orthopaedic plate.
Figure 16A:
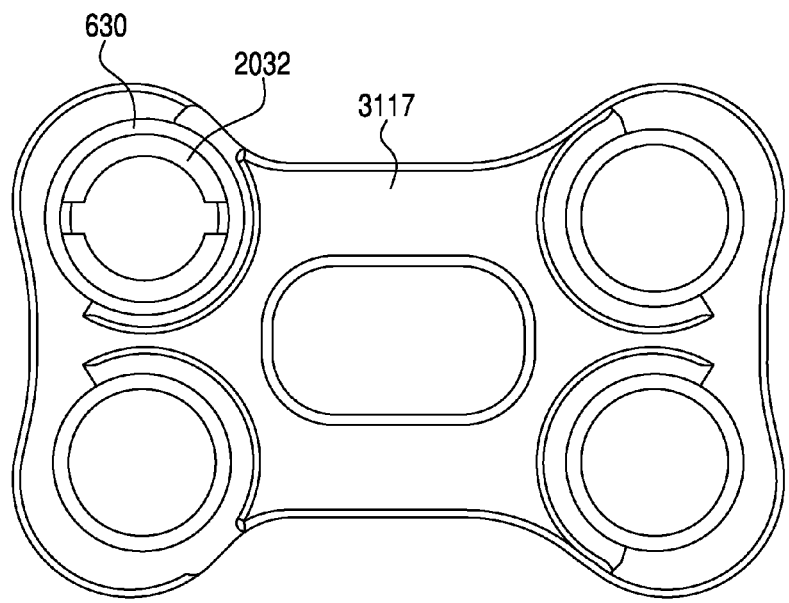
FIG. 16A is a top view of an orthopaedic device having an orthopaedic plate, a tissue protector and a rotating member.
Figure 16B:
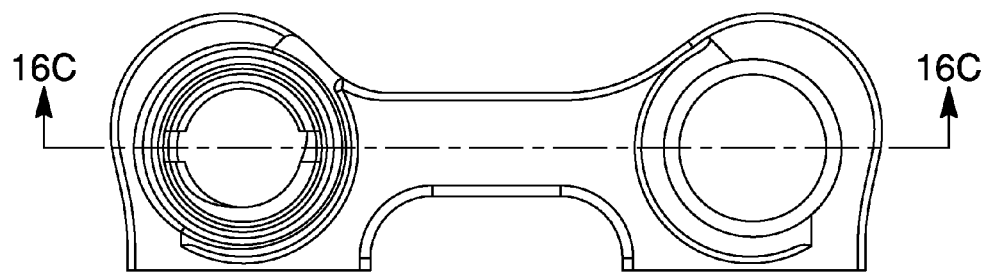
FIG. 16B is a partial top view of the orthopaedic device of FIG. 16A.
Figure 16C:
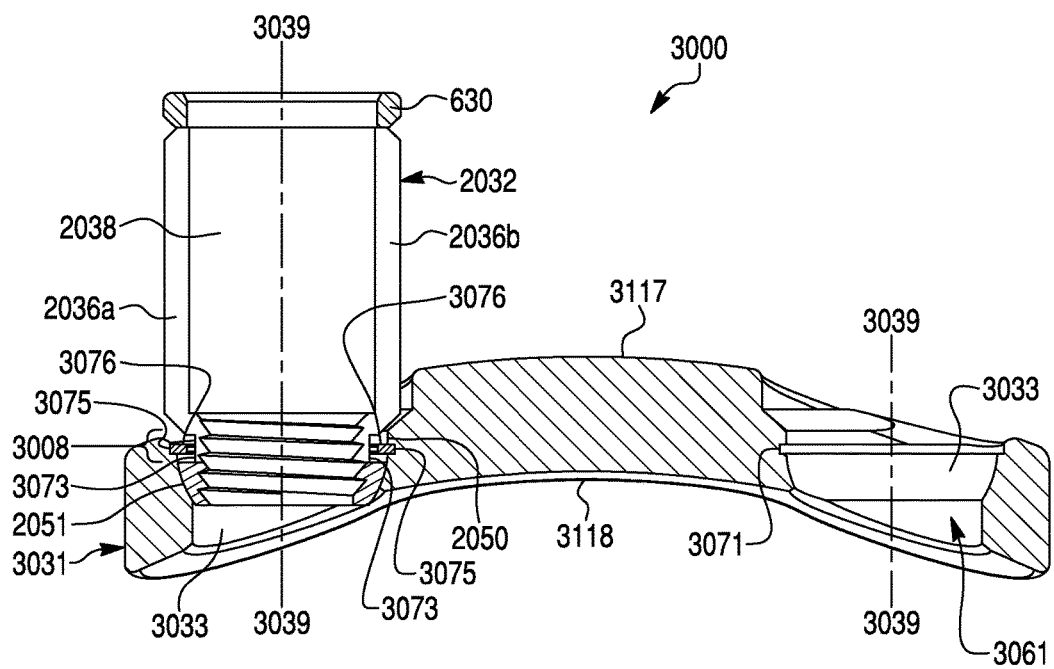
FIG. 16C is a cross section of the orthopaedic device of FIG. 16B taken along line 16C-16C

The orthopaedic device 2000, 3000 with the rotating member 2060, 3060 may also include an orthopaedic plate surface 2050 (FIGS. 14A, 14B and 16C) within an interior 2061, 3061 (FIGS. 14A, 14B and 16C) of the orthopaedic plate. The orthopaedic plate surface 2050 is substantially a mirror image of a tissue protector surface 2051 (FIGS. 14A, 14B and 16C) that is on an outer surface of the tissue protector such that the tissue protector surface 2051 moves relative to the orthopaedic plate surface 2050 when the tissue protector 2032 rotates. For example, the orthopaedic plate surface 2050 and tissue protector surface 2051 may each be semi-spherical or substantially semi-spherical. When these surfaces 2050, 2051 are semi-spherical or substantially semi-spherical the orthopaedic plate surface 2050 may be concave or substantially concave and the tissue protector surface 2050 may be convex or substantially convex (FIGS. 14 and 16C). Alternatively, the orthopaedic plate surface 2050 may be concave or substantially concave and the tissue protector surface 2050 may be convex or substantially convex.

The rotating member 2060, 3060 may be any suitable element that can allow the tissue protector to rotate relative to the orthopaedic plate when a clamp or other suitable mechanism, such as described further herein, is applied to the tissue protector or when a person manually adjusts the tissue protector. For example, the rotating member may comprise a pin mechanism 2060 (FIGS. 13-15B) or a retaining ring mechanism 3060 (FIGS. 16A-20).

The pin mechanism 2060 (FIGS. 13-15B) may allow the tissue protector 2032 to rotate in a single plane extending along the longitudinal axis 2039-2039 of the hole 2033 in the orthopaedic plate 2031 (FIGS. 13-15B). Specifically, the pin mechanism 2060 may allow the tissue protector 2032 to rotate a tissue protector angle 2081 (FIGS. 15A-15B) that is clockwise or counterclockwise from the longitudinal axis 2039-2039. The tissue protector angle 2081 may range from 5 degrees or about 5 degrees counterclockwise (FIG. 15A) to 5 degrees or about 5 degrees clockwise (FIG. 15B) from the longitudinal axis 2039-2039. Alternatively, the tissue protector angle 2081 may range from 10 or about 10 degrees counterclockwise to 10 degrees or about 10 degrees clockwise from the longitudinal axis 2039-2039. When the tissue protector 2032 is not rotated relative to the orthopaedic plate 2031 (i.e., the tissue protector 2032 is 0 degrees from the longitudinal axis 2039-2039), the tissue protector longitudinal axis 2009-2009 (FIGS. 13-14) of the tissue protector 2032 is the same as the longitudinal axis 2039-2039 of the orthopaedic plate. When the tissue protector 2032 rotates relative to the orthopaedic plate 2031, the tissue protector longitudinal axis 2009-2009 is at a tissue protector angle 2081 to the longitudinal axis 2039-2039 of the orthopaedic plate.

The pin mechanism 2060 is rotatably fixed to the orthopaedic plate 2031 and rotates relative to the tissue protector 2032, or rotatably fixed relative to the tissue protector 2032 and rotates relative to the orthopaedic plate 2031 (FIGS. 13-15b). Preferably the pin mechanism 2060 is rotatably fixed relative to the orthopaedic plate 2031 and rotates relative to the tissue protector 2032 because it may be easier to manufacture the orthopaedic device 2000 when the pin mechanism 2060 is rotatably fixed to the orthopaedic plate 2031 as opposed to when the pin mechanism 2060 is rotatably fixed to the tissue protector 2032. Moreover, preferably the pin mechanism 2060 is rotatably fixed relative to the orthopaedic plate 2031 because if the pin mechanism 2060 is rotatably fixed relative to the tissue protector 2032, the pin mechanism 2060 may loosen from the tissue protector 2032 when the tissue protector leaves 2036a, 2036b detach during placement of the fastener. The pin mechanism 2060 may be rotatably fixed to the orthopaedic plate 2031 or the tissue protector 2032 by any suitable mechanism. For example, the pin mechanism 2060 may be rotatably fixed by welding, gluing, screwing, etc. the pin mechanism 2060 to the orthopaedic plate 2031 or the tissue protector 2032. The pin mechanism 2060 may also be fixed by press-fitting the pin mechanism 2060 to the orthopaedic plate 2031 or the tissue protector 2032 or by using an expandable pin mechanism 2060.

The pin mechanism 2060 includes a first pin mechanism member 2001 and a second pin mechanism member 2002 that is one of substantially the same as and different from the first pin mechanism member 2001. The second pin mechanism member 2002 may be the same as the first pin mechanism member 2001 such that the first and second pin mechanism members 2001, 2002 have the same dimensions or the second pin mechanism member 2002 may be different from the first pin mechanism member 2001 such that the first and second pin mechanism members 2001, 2002 have different dimensions (FIG. 14). The diameter of the first and second pin mechanism members 2001, 2002 may be less than 1 mm or about less than 1 mm and the length of the first and second pin mechanism members 2001, 2002 may range from 2-6 mm or about 2-6 mm. When the first and second pin mechanism members 2001, 2002 are different, the second pin mechanism member 2002 may extend from one opening 2033 in the orthopaedic plate 2031 to another opening 2033 in the orthopaedic plate 2031 (FIGS. 13-14).

The first pin mechanism member 2001 is disconnected from the second pin mechanism member 2002. The first and second pin mechanism members 2001, 2002 are separate members that are completely disconnected from each other. The first and second pin mechanism members 2001, 2002 are separated by the opening 2038 in the tissue protector 2032 (FIG. 13). The first and second pin mechanism members 2001, 2002 may be in-line or substantially in-line with each other such that they are substantially 180 or 180 degrees apart. Alternatively, the first and second pin mechanism members 2001, 2002 may be more than 180 degrees apart.

The first and second pin mechanism members 2001, 2002 may extend along the shorter width of the orthopaedic plate 2031 (FIG. 13) or the longer width of the orthopaedic plate 2031. When the first and second pin mechanism members 2001, 2002 extend along the shorter width of the orthopaedic plate 2031, the tissue protector 2032 rotates about a longitudinal axis of the pin mechanism member 2001, 2002 whose plane extends along the longer width of the orthopaedic plate 2031 (i.e., the rotation would be in a saggital plane that would allow a user to direct the fasteners up or down). When the first and second pin mechanism members 2001, 2002 extend along the longer width of the orthopaedic plate 2031, the tissue protector 2032 rotates about a longitudinal axis 2009-2009 of the pin mechanism member 2001, 2002 whose plane extends along the narrower width of the orthopaedic plate (i.e., the rotation would be in a transverse plane that allows a surgeon to direct the fasteners in a medial or lateral direction).

The first and second pin mechanism members 2001, 2002 may be partially within first and second pin mechanism member plate openings 2011, 2012, respectively, (FIG. 13) included in the orthopaedic plate 2031. The first pin mechanism member plate opening 2011 may be one of a same size and a different size from the second pin mechanism member plate opening 2012. The size of the first and second pin mechanism member plate openings 2011, 2012 depends on the dimensions of the first and second pin mechanism members 2001, 2002. Thus, the first and second pin mechanism member plate openings 2011, 2012 are likely the same size if the first and second mechanism members 2001, 2002 are the same size and the first and second pin mechanism member plate openings 2011, 2012 are likely a different size if the first and second mechanism members 2001, 2002 are a different size. In general, the first and second pin mechanism member plate openings 2011, 2012 are dimensioned so that there is enough of a clearance between the diameter of the first and second pin mechanism member plate openings 2011, 2012 and the diameter 2001a, 2002b (FIG. 13) of the first and second pin members 2001, 2002 to allow the first and second pin members 2001, 2002 to rotate within the first and second pin mechanism member plate openings 2011, 2012. The orthopaedic plate may include additional openings 2013, each for receiving a pin mechanism member, that are the same or different size from the first and/or second pin mechanism member plate openings.

The first and second pin mechanism members 2001, 2002 may partially fit within openings within the tissue protector 2032 or may extend from an outer surface of the tissue protector 2032. For example, as shown in FIG. 14A, the tissue protector 2032 may include a first pin mechanism member tissue protector opening 2091 and a second pin mechanism member tissue protector opening 2092 where the first pin mechanism member 2001 is partially within the first pin mechanism member tissue protector opening 2091 and the second pin mechanism member 2002 is partially within the second pin mechanism member tissue protector opening 2092. The first pin mechanism member plate opening 2001 may be substantially in-line or in-line with the first pin mechanism member tissue protector opening 2091 such that they are substantially 180 or 180 degrees apart and the second pin mechanism member tissue protector opening 2002 may be substantially in-line or in-line with the second pin mechanism member tissue protector opening 2092 such that they are substantially 180 or 180 degrees apart. Alternatively, the tissue protector 2032 may not include any first and second pin mechanism member tissue protector openings 2091, 2092 (FIG. 14B). When the tissue protector 2032 does not include such openings and the first and second pin mechanism members 2001, 2002 connect to the tissue protector 2032, the first and second pin mechanism members 2001, 2001 may connect to an outer surface 2053 of the tissue protector 2032.

When the pin mechanism 2060 is rotatably fixed relative to the orthopaedic plate 2031 and rotates relative to the tissue protector 2032, the first and second pin mechanism members 2001, 2002 extend from a hole/opening 2011, 2012, 2013 (FIG. 13) in the orthopaedic plate 2031 to a hole/opening 2091, 2092 (FIG. 14A) in the tissue protector 2032. Because the pin mechanism members 2001, 2002 are rotatable fixed relative to the orthopaedic plate 2031, the pin mechanism members 2001, 2002 remain stationary while the tissue protector 2032 rotates. When the pin mechanism members 2060 are rotatably fixed relative to the tissue protector 2032, the first and second pin mechanism members 2001, 2002 extend from an opening 2011, 2012, 2013 in the orthopaedic plate 2031 to the opening 2091, 2092 (FIG. 14A) or an outer surface 2053 (FIG. 14B) of the tissue protector 2032. Because the pin mechanism members 2001, 2002 are rotatably fixed relative to the tissue protector 2032, the first and second pin mechanism members 2001, 2002 rotate with the tissue protector 2032 when the tissue protector 2032 rotates. Instead of a hole/opening 2011, 2012, 2012, 2091, 2092, the orthopaedic plate 2031 and/or tissue protector 2032 may include a well or socket.

Figure 17:
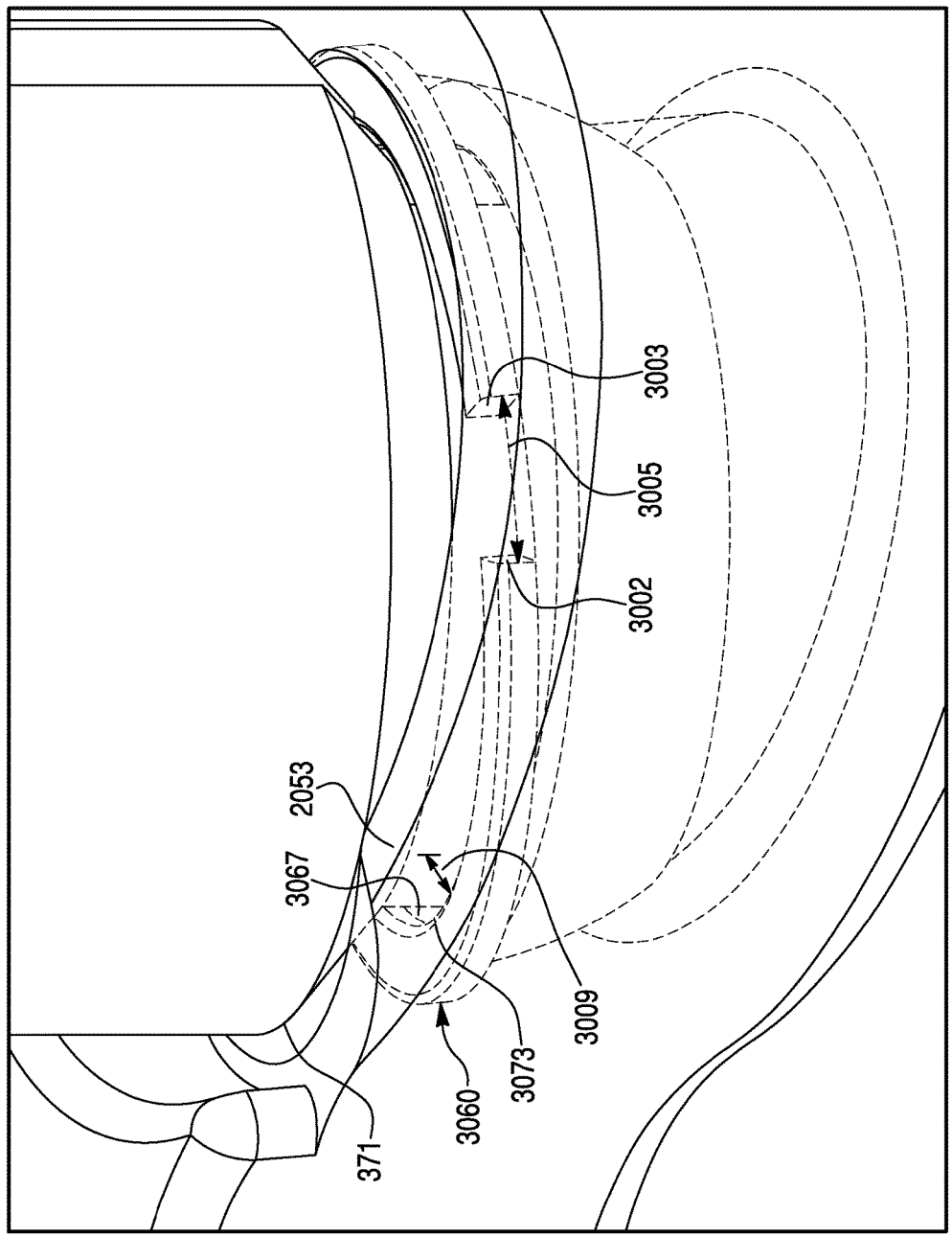
FIG. 17 is a partial side view of the orthopaedic device of FIG. 16A.
Figure 18A:
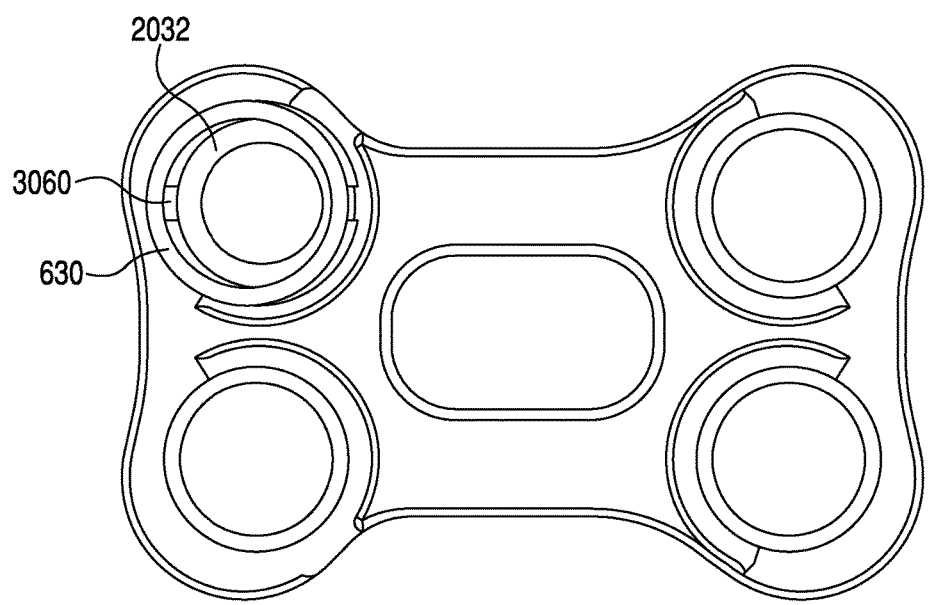
FIG. 18A is a top view of the orthopaedic device of FIG. 16A after the tissue protector has rotated about 2.5 degrees counterclockwise from a longitudinal axis that extends through the orthopaedic plate.
Figure 18B:
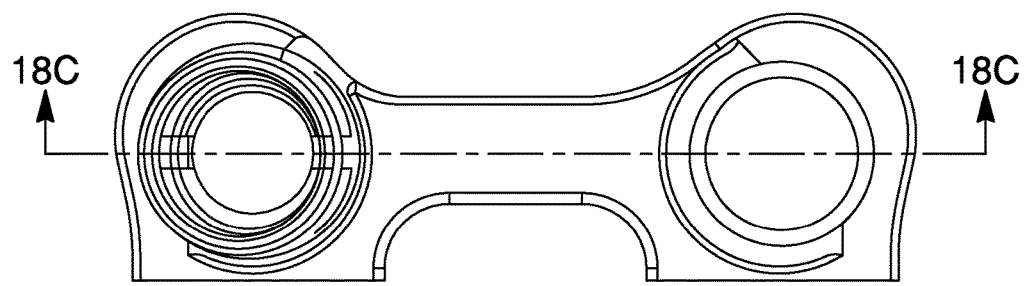
FIG. 18B is a partial top view of the orthopaedic device of FIG. 18A.
Figure 18C:
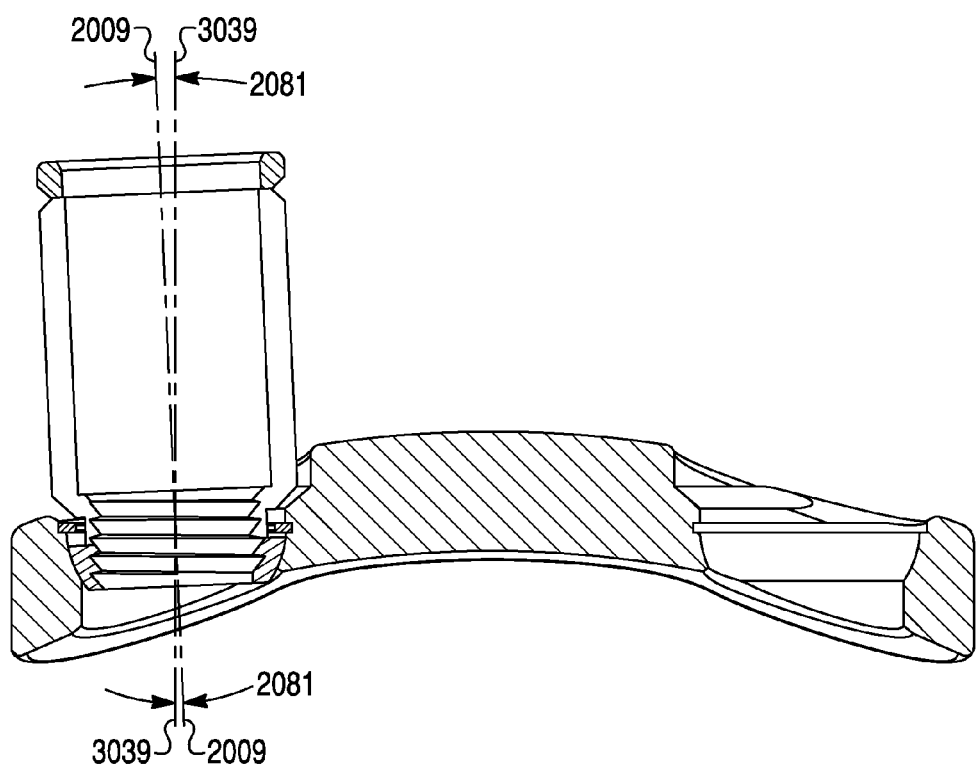
FIG. 18C is a cross-section of the orthopaedic device of FIG. 18B taken along line 18C-18C.
Figure 19A:
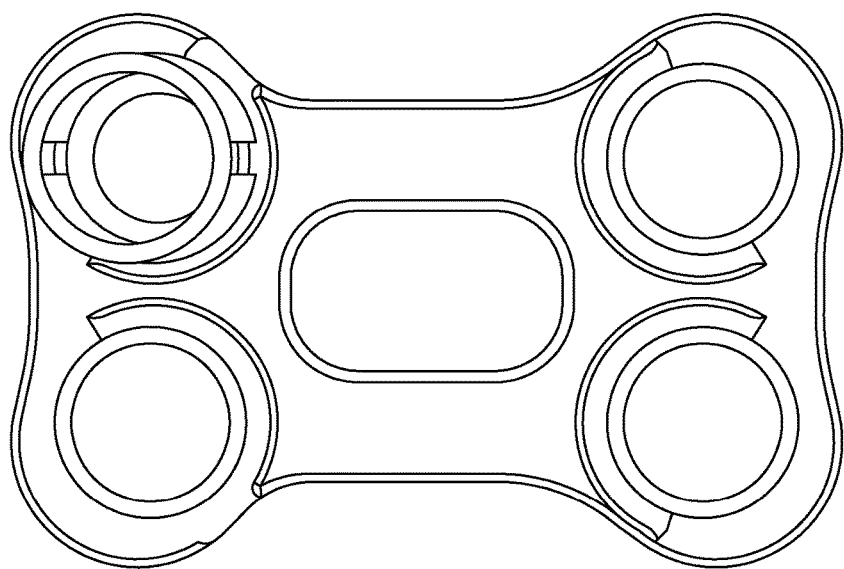
FIG. 19A is a top view of the orthopaedic device of FIG. 16A after the tissue protector has rotated about 5 degrees counterclockwise from a longitudinal axis that extends through the orthopaedic plate
Figure 19B:
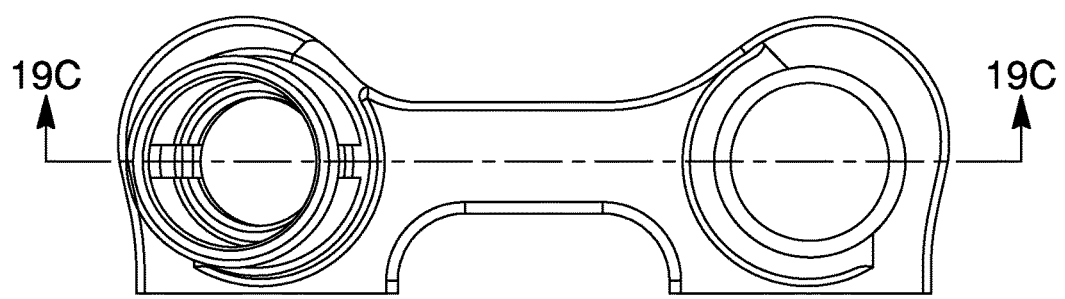
FIG. 19B is a partial top view of the orthopaedic device of FIG. 19A.
Figure 19C:
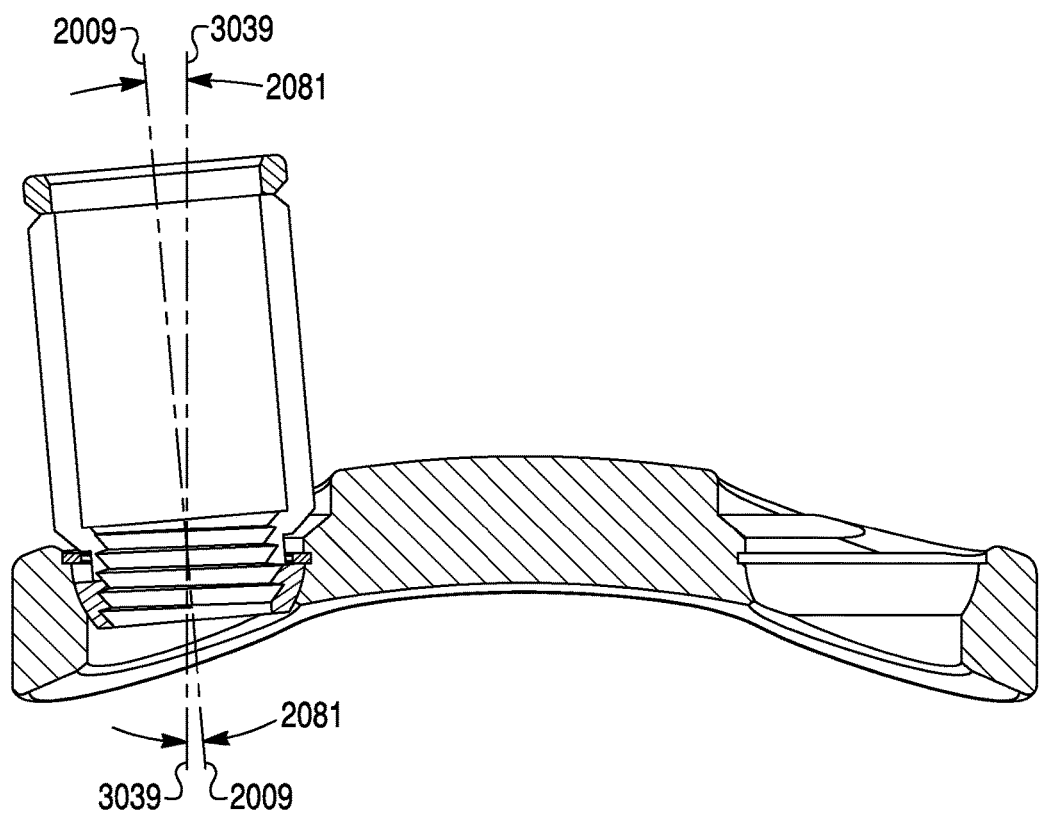
FIG. 19C is a cross-section of the orthopaedic device of FIG. 19B taken along line 19C-19C.
Figure 20:
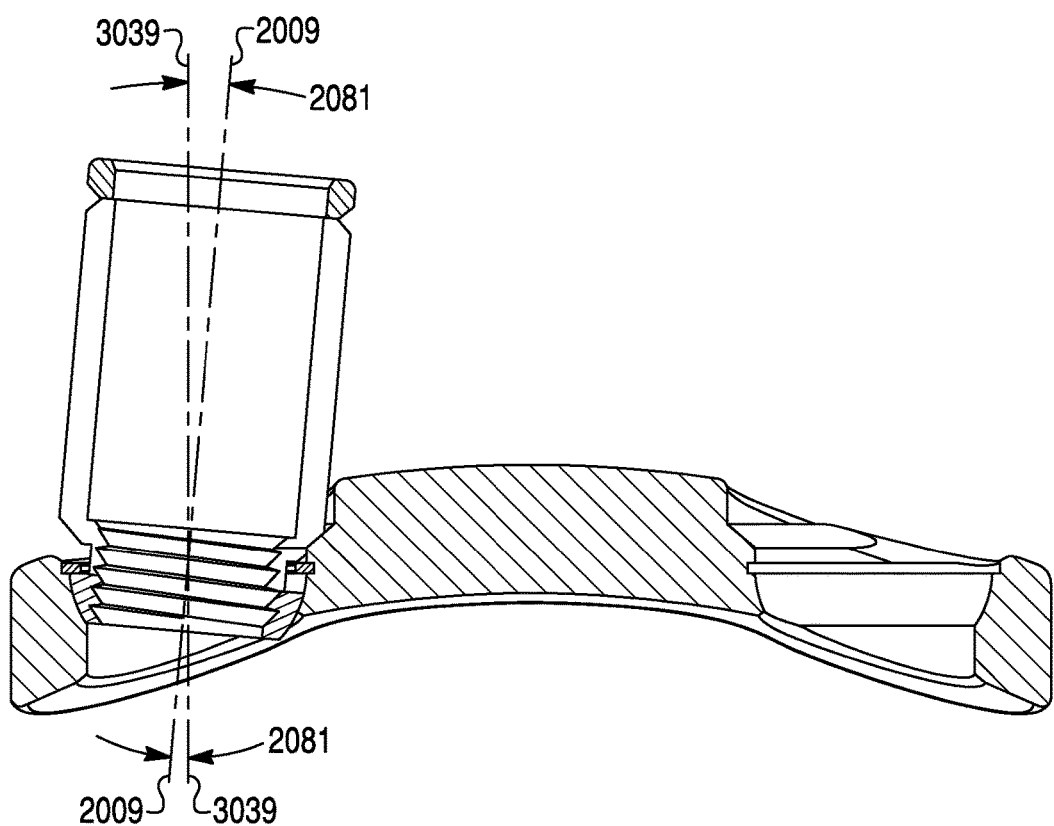
FIG. 20 is a cross-section of the orthopaedic device of FIG. 16A after the tissue protector has rotated about 5 degrees clockwise from a longitudinal axis that extends through the orthopaedic plate.

Unlike the pin mechanism 2060, the retaining ring mechanism 3060 may allow for infinite angulation within 0 to a maximum of about 5 to 10 degrees or 5 to 10 degrees from the longitudinal axis of the hole that extends through the orthopaedic plate and the retaining ring mechanism 3060 may include a first retaining ring mechanism end 3002 (FIG. 17) and a second retaining ring mechanism end 3003 (FIG. 17). The second retaining ring mechanism end 3003 may be disconnected from the first retaining ring mechanism end 3002 such that there is a space 3005 between the first and second retaining ring mechanism ends 3002, 3003 when the retaining ring mechanism 3060 is in a relaxed state.

The retaining ring mechanism 3060 may be any suitable shape and size and may comprise any suitable material that allows the retaining ring mechanism 3060 to expand and contract. Preferably, the retaining ring mechanism 3060 is C-shaped, U-shaped. substantially C-shaped, or substantially U-shaped and comprises a metal such as titanium, stainless steel or cobalt-chrome. The retaining ring mechanism 3060 may have a diameter of 8-10 mm or about 8-10 mm and the height and thickness of the retaining ring mechanism 3060 may be 1 mm or less or about 1 mm or less.

The retaining ring mechanism 3060 may be in the relaxed state or a contracted state. When the retaining ring mechanism 3060 is C-shaped or substantially C-shaped (FIGS. 16A-21), the retaining ring mechanism 3060 may be in the relaxed state when the retaining ring mechanism 3060 is clamped around the tissue protector 2032 and may be in the contracted state when the retaining ring mechanism 3060 is being placed around the tissue protector 2032. When the retaining ring mechanism 3060 is U-shaped or substantially U-shaped (FIGS. 22a-22b), the retaining ring mechanism 3060 may be in the contracted state when the retaining ring mechanism 3060 enters the orthopaedic plate 3031 through a slot 3093 (e.g. opening, hole) in the orthopaedic plate 3031 that extends from an outer surface 3094 of the orthopaedic plate 3031 to the opening 3033 of the orthopaedic plate 3031. When the retaining ring mechanism 3060 is U-shaped or substantially U-shaped, the retaining ring mechanism 3060 may be in the relaxed or contracted state when the retaining ring mechanism 3060 is being placed around the tissue protector 2032.

Figure 21:
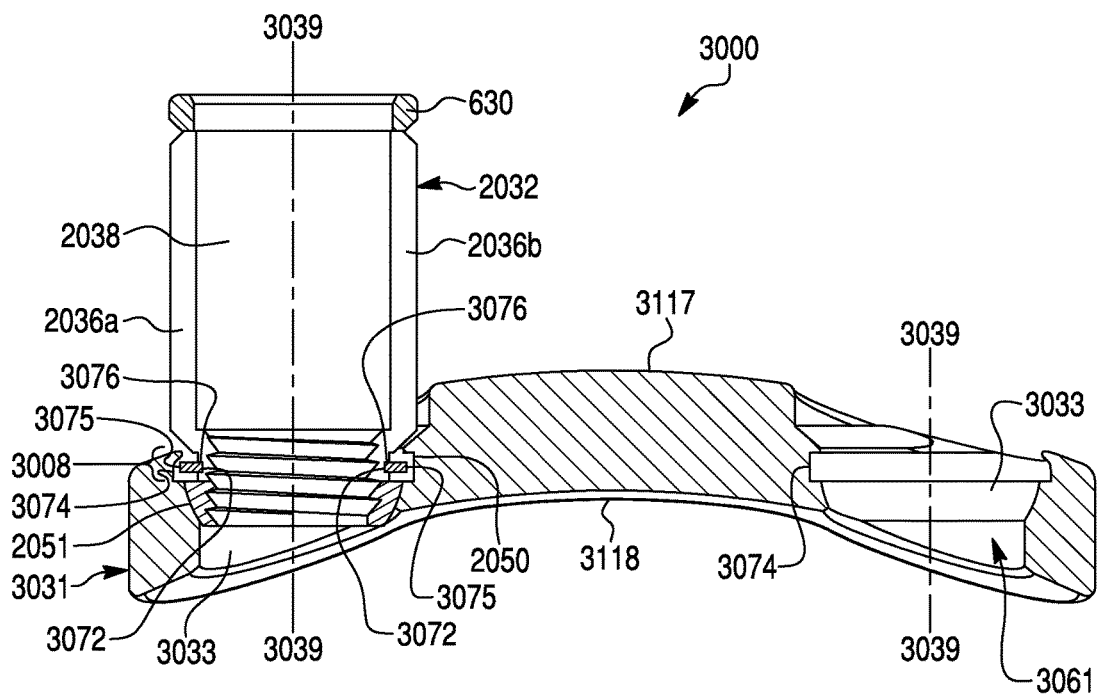
FIG. 21 is a cross-section of an orthopaedic device with a retaining ring mechanism member as a rotating member.
Figure 22A:
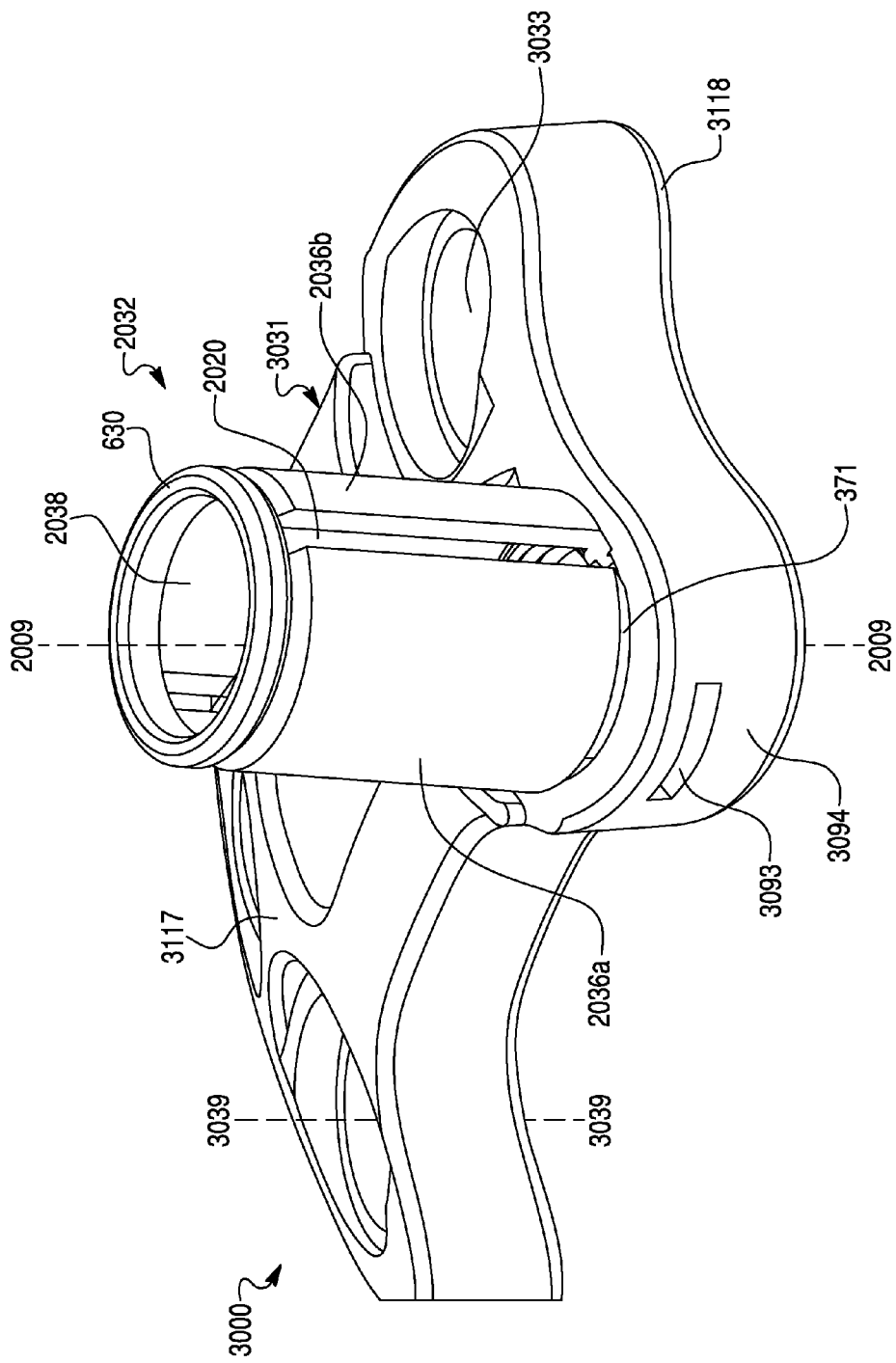
FIG. 22A is a side elevated view of an orthopaedic device having an orthopaedic plate, a tissue protector and a rotating member.
Figure 22B:
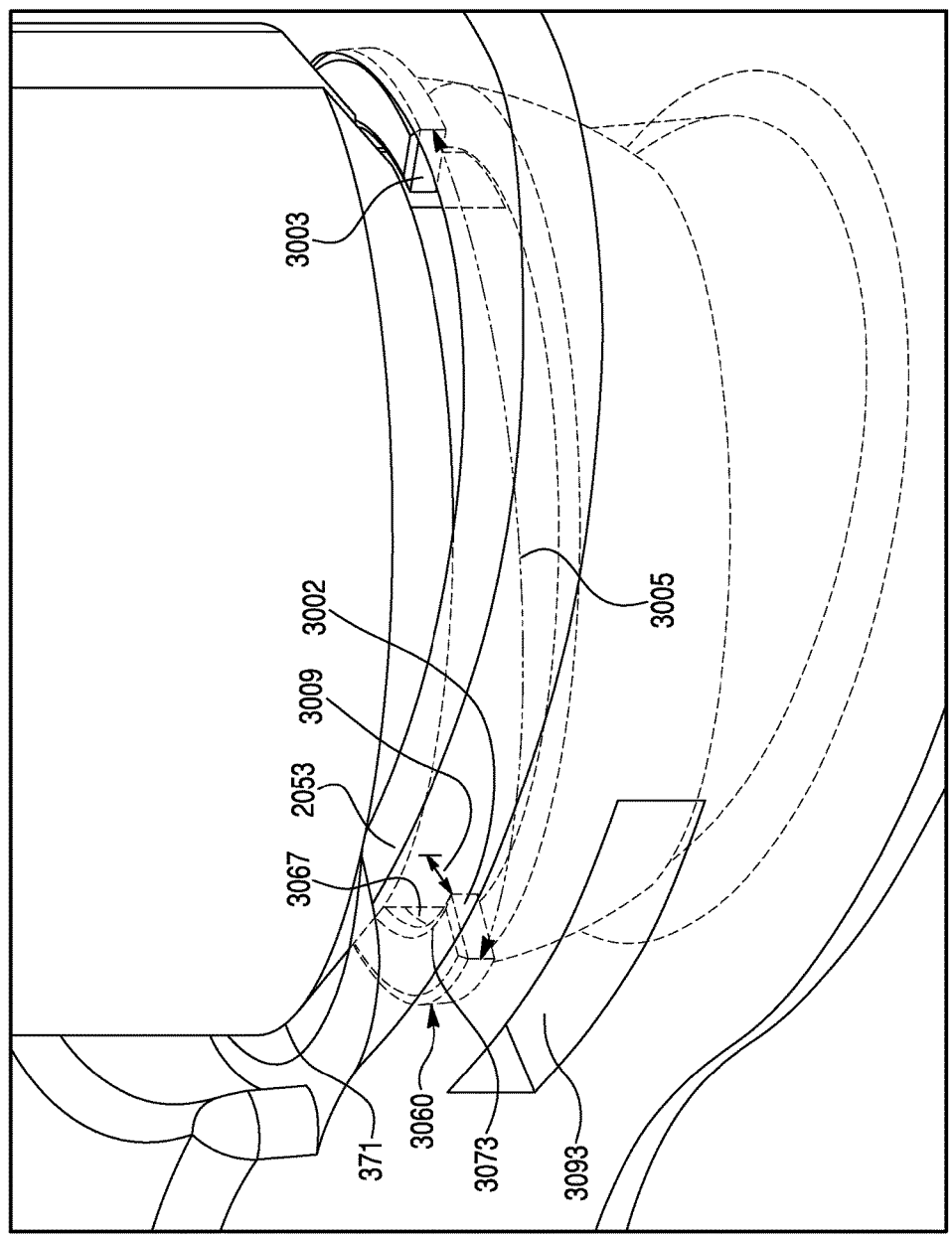
FIG. 22B is a partial side view of the orthopaedic device of FIG. 22A.

When the retaining ring mechanism 3060 is clamped around the tissue protector 2032, a portion or all of the retaining ring mechanism 3060 may fit within a groove 3071 (FIG. 16C) of the orthopaedic plate 3031 or a groove 3072 of the tissue protector 2032 (FIG. 21). The groove 3071, 3072 may be dimensioned so that the retaining ring mechanism 3060 is secured within the groove 3071, 3072 (i.e., there is a tight fit between the groove 3071, 3072 and retaining ring mechanism 3060) once the retaining ring mechanism 3060 is in the relaxed state. Alternatively, the groove 3072 may be dimensioned such that the height (i.e., height along the vertical distance) of the groove 3072 is oversized relative to the height of the retaining ring mechanism 3060 to allow more rotational motion in the orthopaedic plate or tissue protector. When the groove 3071, 3072 is dimensioned so that the retaining ring mechanism 3060 is secured within the groove 3071, 3072, the groove 3071, 3072 height may be about the height of the retaining ring mechanism 3060 in a relaxed state. For example, the groove 2071, 2072 height may be 1 mm or less or about 1 mm or less.

When the groove 3071 is part of the orthopaedic plate 3031 and is dimensioned so that the retaining ring mechanism 3060 is secured within the groove 3071, a first portion 3075 (i.e., an outer side of the retaining ring mechanism) of the relaxed, retaining ring mechanism 3060 may securely fit within the groove 3071 and a second portion 3076 (i.e., an inner side of the retaining ring mechanism) of the relaxed, retaining ring mechanism 3060 may fit inside an opening 3073 in the tissue protector (FIG. 16C) that is dimensioned to be larger than the groove 3071 such that the retaining ring mechanism 3060 may move a maximum vertical distance 3008 within the opening 3073.

When the groove 3072 is part of the tissue protector 2032 and is dimensioned so that the retaining ring mechanism 3060 is secured within the groove 3072, the second portion 3076 of the relaxed, retaining ring mechanism 3060 may securely fit within the groove 3072 and the first portion 3075 of the relaxed, retaining ring mechanism 3060 may fit inside an opening 3074 in the orthopaedic plate (FIG. 21) that is dimensioned to be larger than the groove 3072 such that the retaining ring mechanism 3060 may move a maximum vertical distance 3008 within the opening 3074. The maximum vertical distance may be 2-3 mm or about 2-3 mm.

The retaining ring mechanism 3060 may include a retaining ring mechanism opening 3067 (FIG. 17) that completely extends through a center of the retaining ring mechanism 3067 such that the inner diameter of the retaining ring mechanism 3060 is hollow. When the retaining ring mechanism 3060 is in the expanded shape, a horizontal distance 3009 (FIG. 17) may exist between the edges 3073 (FIG. 17) of the retaining ring mechanism opening 3067 and the outer surface 2053 (FIG. 17) of the tissue protector 2032. When the tissue protector 2032 rotates relative to the orthopaedic plate, the tissue protector 2032 may move a maximum horizontal distance equal to the horizontal distance 3009. The maximum horizontal distance may be 1 mm or less or about 1 mm or less. The tissue protector 2032 may also move a maximum vertical distance equal to the maximum vertical distance 3008 (FIGS. 16C and 21).

A method for repairing parts of a body with an orthopaedic device 100, 200, 300, 400, 600, 700, 800, 900, 1000, 1100, 2000, 3000 having an orthopaedic plate 31, 131, 301, 1101, 2031, 3031 and a tissue protector 32, 232, 332, 632, 732, 832, 932, 1032, 2032 securely attached to the orthopaedic plate 31, 131, 301, 1101, 2031, 3031 may include first placing the orthopaedic plate 31, 131, 301, 1101, 2031, 3031 on the part of the body. The part of the body may be at least one bone. An awl (e.g. punch awl) may be used to place the orthopaedic plate 31, 131, 301, 1101, 2031, 3031 on the part of the body. The awl is able to fit within the openings of the orthopaedic plate and the openings of the tissue protector where the tissue protector may act as a guide for the awl. Instead of an awl, a drill or pin may be used to place the orthopaedic plate 31, 131, 301, 1101, 2031, 3031 on the part of the body and, like the awl, the drill and pin are able to fit within the openings of the orthopaedic plate and the openings of the tissue protector where the tissue protector may act as a guide for the drill or pin. The tissue protectors may also act as a guide for a drill or a tap that may be used to prepare a hole in at least one bone for receiving the fastener. Additionally or alternatively, the tissue protectors may swivel or angulate so that a user (e.g., surgeon) may determine the preferred trajectory for the awl and subsequently the fastener.

Before or after positioning the orthopaedic plate 31, 131, 301, 1101, 2031, 3031 on the part of the body, the tissue protector 32, 232, 332, 632, 732, 832, 932, 1032, 2032 may be attached to the orthopaedic plate 31, 131, 301, 1101, 2031, 3031. When the orthopaedic device 100, 200, 300, 400, 600, 700, 800, 900, 1000, 1100, 2000, 3000 includes a rotating member 2060, 3060, the rotating member 2060, 3060 may be positioned within openings 2091, 2092 in the tissue protector 2032 and/or openings 2001, 2002 in the orthopaedic plate, or around the tissue protector 2032 before the tissue protector 2032 is securely attached to the orthopaedic plate 2031, 3031. When the rotating member 2060 is positioned within openings 2091, 2092 in the tissue protector 2032 and/or openings 2001, 2002 in the orthopaedic plate 2031, the rotating member 2060 may be attached to the orthopaedic plate 2031 or tissue protector 2032 before the tissue protector 2032 is securely attached to the orthopaedic plate 2031, 3031.

Before or after positioning the orthopaedic plate 31, 131, 301, 1101, 2031, 3031 on the part of the body, each opening 33, 303, 333, 403, 2033, 3033 of the orthopaedic plate 31, 131, 301, 1101, 2031, 3031 may or may not be threaded using any suitable mechanism (e.g. manually or automatically). One or more fasteners 304 are fastened into the tissue protector(s) 32, 232, 332, 632, 732, 832, 932, 1032, 2032 and then the orthopaedic plate 31, 131, 301, 1101, 2031, 3031. Each of the fasteners 304 may be fastened by fastening (e.g. screwing) the fastener 304 into one of the tissue protectors 32, 232, 332, 632, 732, 832, 932, 1032, 2032 and the orthopaedic plate 31, 131, 301, 1101, 2031, 3031. The fastener 304 is fastened to the orthopaedic plate 31, 131, 301, 1101, 2031, 3031 by being inserted into the opening 38, 58, 338, 408, 508, 2038 of the tissue protector 32, 232, 332, 632, 732, 832, 932, 1032, 2032 and once inserted, fastening to the tissue protector 32, 232, 332, 632, 732, 832, 932, 1032, 2032 and then to the orthopaedic plate 31, 131, 301, 1101, 2031, 3031. If the orthopaedic device includes a rotating member 2060, 3060, the fastener 304 may be at an angle to a longitudinal axis of the orthopaedic plate when it enters the tissue protector if the rotating member 2060, 3060 causes the tissue protector to be at an angle to a longitudinal axis of the orthopaedic plate.

A substantial portion or all of the tissue protectors 32, 232, 332, 632, 732, 832, 932, 1032, 2032 may detach from the orthopaedic plate 31, 131, 231, 301, 2031, 3031 when a force, such as a substantial force, is applied to the tissue protector(s) 32, 232, 332, 632, 732, 832, 932, 1032, 2032 by a clamp or other suitable mechanism, such as described further herein. Specifically, the tissue protector(s) 32, 232, 332, 632, 732, 832, 932, 1032, 2032 detach when the force is applied or exerted on the thinned section 371 by a clamp or other suitable mechanism, such as described further herein. The force is preferably not applied until after the fastener 304 is completely fastened to the orthopaedic plate 31, 131, 301, 1101, 2031, 3031 and the relevant portion of the body.

The force may be exerted by using a clamp to grab an individual leaf 36a, 36b, 56a, 56b, 366a, 366b, 406a, 406b, 506a, 506b, 505a, 505b, 605a, 605b, 2036a, 2036b and, after grabbing the leaf, bending or twisting the leaf 36a, 36b, 56a, 56b, 366a, 366b, 406a, 406b, 506a, 506b, 505a, 505b, 605a, 605b, 2036a, 2036b until enough force has been exerted on the thinned section 371 to cause the leaf to detach from the orthopaedic plate. In addition to bending and/or twisting (rotating), one can place a cylindrical device inside the tissue protector that can radially expand outward to shear the leaves off at the thinned section 371 or notched region. Outward expansion may be due to advancement of a device through the tissue protector that has a larger diameter than the inner diameter of the tissue protector at its thinned section. Tissue protector detachment by shearing may also be performed by rotation about the hole axis (i.e. the longitudinal axis of the tissue protector). This device may be combined with a clamp to retrieve the leaves from the surgical field. The leaves 36a, 36b, 56a, 56b, 366a, 366b, 406a, 406b, 506a, 506b, 505a, 505b, 605a, 605b, 2036a, 2036b may be detached from the orthopaedic plate at different times or simultaneously. The force may also be exerted by a fastener whose threads exert a force on the leaves by cutting through a thinned section of the tissue protector.

In the case of a semi-conically shaped tissue protector 932 the suitable force may be exerted by a slightly oversized fastener head. A slightly oversized fastener head may be one that has a slightly larger diameter than the opening of the tissue protector. When a slightly oversized fastener head fits into the opening (not shown) of the tissue protector 932 and advances through the tissue protector 932 and into the orthopaedic plate 301, the fastener head abuts the inside aspect of a narrower (smaller inner diameter near the orthopaedic plate) portion 65 (FIG. 9A) of the tissue protector 932 just before the fastener 304 is fully seated. The interaction between the narrower portion 65 of the tissue protector 932 and the fastener 304 causes the thinned section 371 to shear away from the orthopaedic plate 301. While a slightly oversized fastener head is discussed in terms of being used for a semi-conically shaped tissue protector, the slightly oversized fastener head may be used for other shaped tissue protectors (e.g. semi-cylindrically shaped tissue protector).

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure.

It is recognized that features of the disclosed embodiments can be incorporated into other disclosed embodiments.

It is important to note that the construction and arrangement of the orthopaedic device as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosure herein. For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes and omissions may be made in the design, operating conditions and arrangement of the exemplary embodiments.

What is claimed is:

1. An orthopaedic device for repairing a portion of a body, the orthopaedic device comprising:
    an orthopaedic plate configured to attach to at least one bone and having a hole;
    a tissue protector attached to the orthopaedic plate and configured to at least partially detach from the orthopaedic plate after a force is applied to the tissue protector; and
    a rotating member that is configured to connect the tissue protector to the orthopaedic plate while allowing the tissue protector to rotate relative to the orthopaedic plate such that a longitudinal axis extending through the tissue protector can be positioned at an angle relative a longitudinal axis extending through the hole of the orthopaedic plate,
    wherein the rotating member comprises a retaining ring mechanism,
    wherein the retaining ring mechanism is positioned around a portion of the tissue protector and a gap is formed between an inner surface of the retaining ring mechanism and an outer surface of the tissue protector.

2. The orthopaedic device of claim 1,
wherein the orthopaedic plate includes an orthopaedic plate surface within an interior of the orthopaedic plate that is substantially semi-spherical, and
wherein the tissue protector includes a tissue protector surface on the outer surface of the tissue protector that is semi-spherical and abuts the orthopaedic plate surface.

3. The orthopaedic device of claim 2, wherein one of (i) the orthopaedic plate surface is substantially concave and the tissue protector surface is substantially convex and (ii) the orthopaedic plate surface is substantially convex and the tissue protector surface is substantially concave.

4. The orthopaedic device of claim 1, wherein the rotating member is within the orthopaedic plate.

5. The orthopaedic device of claim 1, wherein the retaining ring mechanism includes a first retaining ring mechanism end and a second retaining ring mechanism end that is disconnected from the first retaining ring mechanism end such that there is a space between the first and second retaining ring mechanism ends.

6. The orthopaedic device of claim 1, wherein the retaining ring mechanism is substantially C-shaped.

7. The orthopaedic device of claim 1, wherein the retaining ring mechanism includes a retaining ring mechanism opening that completely extends through a center of the retaining ring mechanism.

8. The orthopaedic device of claim 1, wherein one of the orthopaedic plate and the tissue protector includes a groove, and wherein a portion of the retaining ring mechanism is within the groove.

9. The orthopaedic device of claim 1,
wherein one of (i) the orthopaedic plate includes a groove and the tissue protector includes an opening and (ii) the tissue protector includes a groove and the orthopaedic plate includes an opening, and
wherein the retaining ring mechanism is within the groove and the opening.

10. The orthopaedic device of claim 1, wherein the gap creates a horizontal distance between the inner surface of the retaining ring and the outer surface of the tissue protector.

11. The orthopaedic device of claim 1, wherein the tissue protector is configured to move a maximum horizontal distance that is equal to the horizontal distance created by the gap.

* * * * *